(12) United States Patent
Montello et al.

(10) Patent No.: US 11,389,209 B2
(45) Date of Patent: Jul. 19, 2022

(54) SURGICAL PLATING SYSTEMS, DEVICES, AND RELATED METHODS

(71) Applicant: Medos International Sarl, Le Locle (CH)

(72) Inventors: Albert Montello, Duxbury, MA (US); William Miller, Middleboro, MA (US); Joshua Rodriguez, Raynham, MA (US); Kevin Lee, Canton, MA (US); Veronique Christine Zollmann, Gebenstorf (CH); Laura Wilson, Basel (CH); Roger Berger, Büren (CH); Hyun Bae, Santa Monica, CA (US); Michael Jeger, Oberdorf (CH)

(73) Assignee: Medos International Sarl, Le Locle (CH)

(*) Notice: Subject to any disclaimer, the term of this patent is extended or adjusted under 35 U.S.C. 154(b) by 271 days.

(21) Appl. No.: 16/517,439

(22) Filed: Jul. 19, 2019

(65) Prior Publication Data

US 2021/0015524 A1  Jan. 21, 2021

(51) Int. Cl.
*A61B 17/70* (2006.01)
*A61B 17/80* (2006.01)

(52) U.S. Cl.
CPC ........ *A61B 17/7059* (2013.01); *A61B 17/808* (2013.01); *A61B 17/8057* (2013.01); *A61B 17/8085* (2013.01)

(58) Field of Classification Search
CPC .. A61B 17/0206; A61B 17/7059; A61B 17/80
See application file for complete search history.

(56) References Cited

U.S. PATENT DOCUMENTS

| 4,957,497 A | 9/1990 | Hoogland et al. |
| 5,139,498 A | 8/1992 | Astudillo Ley |

(Continued)

FOREIGN PATENT DOCUMENTS

| CN | 1154441 C | 6/2004 |
| CN | 101778604 A | 7/2010 |

(Continued)

OTHER PUBLICATIONS

U.S. Appl. No. 13/437,792, filed Apr. 2, 2012, Posterior Vertebral Plating System.

(Continued)

*Primary Examiner* — David W Bates
(74) *Attorney, Agent, or Firm* — Barnes & Thornburg LLP

(57) ABSTRACT

Surgical plating systems, devices, and related methods for stabilizing and immobilizing portions of a body for surgical procedures, e.g., spinal surgery, are disclosed herein. The plating systems can have narrow profiles that minimize trauma to the patient. An exemplary bone plating system can include a bone plate having one or more holes for receiving attachment members to couple the bone plate to a bony structure. The plating system can provide multipoint fixation to anatomical structures of the patient to prevent unwanted migration of the bone plate and/or unintentional back-out of the attachment members. In some embodiments, the attachment members can be disposed at various trajectories and angles relative to plating structures and can include a mesh construct and/or additional locking features. In some embodiments, the plating system can be introduced into the patient via an access tube to further limit the invasiveness of the procedure.

24 Claims, 15 Drawing Sheets

(56) References Cited

U.S. PATENT DOCUMENTS

| | | |
|---|---|---|
| 5,275,601 A | 1/1994 | Gogolewski et al. |
| 5,372,598 A | 12/1994 | Luhr et al. |
| 5,531,746 A | 7/1996 | Errico et al. |
| 5,558,674 A | 9/1996 | Heggeness et al. |
| 5,616,144 A | 4/1997 | Yapp et al. |
| 5,647,872 A | 7/1997 | Gilbert et al. |
| 5,653,708 A | 8/1997 | Howland |
| 5,709,686 A | 1/1998 | Talos et al. |
| 5,718,705 A | 2/1998 | Sammarco |
| 5,954,724 A * | 9/1999 | Davidson .............. A61L 31/022 606/76 |
| 6,036,719 A | 3/2000 | Meilus |
| 6,093,188 A | 7/2000 | Murray |
| 6,096,040 A | 8/2000 | Esser |
| 6,206,881 B1 | 3/2001 | Frigg et al. |
| 6,217,578 B1 | 4/2001 | Crozet et al. |
| 6,322,562 B1 | 11/2001 | Wolter et al. |
| 6,364,883 B1 | 4/2002 | Santilli |
| 6,592,586 B1 | 7/2003 | Michelson |
| 6,623,486 B1 * | 9/2003 | Weaver .............. A61B 17/8625 606/291 |
| 6,669,700 B1 | 12/2003 | Farris et al. |
| 6,890,335 B2 | 5/2005 | Grabowski et al. |
| 6,955,677 B2 | 10/2005 | Dahners |
| 6,974,461 B1 | 12/2005 | Wolter |
| 7,128,744 B2 | 10/2006 | Weaver et al. |
| 7,166,111 B2 | 1/2007 | Kolb et al. |
| 7,169,150 B2 | 1/2007 | Shipp et al. |
| 7,223,269 B2 | 5/2007 | Chappuis |
| 7,341,587 B2 | 3/2008 | Molz, IV et al. |
| 7,618,441 B2 | 11/2009 | Groiso |
| 7,637,928 B2 | 12/2009 | Fernandez |
| 7,666,208 B1 | 2/2010 | Asfora |
| 7,695,500 B2 | 4/2010 | Markworth |
| 7,744,630 B2 | 6/2010 | Lancial |
| 7,776,076 B2 | 8/2010 | Grady, Jr. et al. |
| 7,806,911 B2 | 10/2010 | Peckham |
| 7,901,433 B2 | 3/2011 | Forton et al. |
| 7,942,912 B2 | 5/2011 | Brockmeyer et al. |
| 7,976,570 B2 | 7/2011 | Wagner et al. |
| 8,025,677 B2 | 9/2011 | Freid et al. |
| 8,048,076 B2 | 11/2011 | Michelson |
| 8,070,782 B2 | 12/2011 | McKay |
| 8,088,148 B2 | 1/2012 | Falahee |
| 8,097,021 B1 | 1/2012 | Kornel |
| 8,100,946 B2 | 1/2012 | Strausbaugh et al. |
| 8,105,366 B2 | 1/2012 | Null et al. |
| 8,231,661 B2 | 7/2012 | Carls et al. |
| 8,262,696 B2 | 9/2012 | Falahee |
| 8,282,681 B2 | 10/2012 | McLeod et al. |
| 8,343,194 B2 | 1/2013 | Aflatoon |
| 8,343,196 B2 | 1/2013 | Schneider |
| 8,366,748 B2 | 2/2013 | Kleiner |
| 8,485,413 B2 | 7/2013 | Scheib et al. |
| 8,491,633 B2 | 7/2013 | Pasquet et al. |
| 8,517,239 B2 | 8/2013 | Scheib et al. |
| 8,623,020 B2 | 1/2014 | Kim et al. |
| 8,623,062 B2 | 1/2014 | Kondrashov |
| 8,696,707 B2 | 4/2014 | Sutterlin, III |
| 8,715,321 B2 | 5/2014 | Butler et al. |
| 8,758,344 B2 | 6/2014 | Michelson |
| 8,845,697 B2 | 9/2014 | Montello et al. |
| 8,870,882 B2 | 10/2014 | Kleiner |
| 8,951,254 B2 | 2/2015 | Mayer et al. |
| 8,974,497 B2 | 3/2015 | Cho et al. |
| 8,986,305 B2 | 3/2015 | Aflatoon et al. |
| 8,992,579 B1 | 3/2015 | Gustine et al. |
| 9,011,491 B2 | 4/2015 | Carl et al. |
| 9,011,492 B2 | 4/2015 | McCormack et al. |
| 9,060,787 B2 | 6/2015 | Blain et al. |
| 9,101,410 B1 | 8/2015 | Urrea |
| 9,107,708 B2 | 8/2015 | Robinson |
| 9,179,911 B2 | 11/2015 | Morgan et al. |
| 9,433,443 B2 | 9/2016 | Montello et al. |
| 9,763,704 B2 | 9/2017 | Hawkins et al. |
| 9,956,009 B1 | 5/2018 | Shoshtaev |
| 10,045,799 B2 | 8/2018 | Montello et al. |
| 2003/0055429 A1 | 3/2003 | Ip et al. |
| 2004/0034356 A1 * | 2/2004 | LeHuec .............. A61B 17/7059 606/914 |
| 2004/0260306 A1 * | 12/2004 | Fallin .............. A61B 17/866 606/104 |
| 2005/0182408 A1 | 8/2005 | Pfefferle et al. |
| 2005/0267480 A1 | 12/2005 | Suddaby |
| 2006/0004363 A1 | 1/2006 | Brockmeyer et al. |
| 2006/0036250 A1 | 2/2006 | Lange et al. |
| 2006/0235397 A1 | 10/2006 | Sanders et al. |
| 2006/0241597 A1 | 10/2006 | Mitchell et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2007/0123885 A1 * | 5/2007 | Kirschman .......... A61F 2/4465 606/279 |
| 2007/0260244 A1 | 11/2007 | Wolter |
| 2007/0276367 A1 | 11/2007 | Puno |
| 2008/0033437 A1 | 2/2008 | Shipp et al. |
| 2008/0033557 A1 | 2/2008 | Pasquet et al. |
| 2008/0097448 A1 | 4/2008 | Binder et al. |
| 2008/0132954 A1 | 6/2008 | Sekhon et al. |
| 2008/0140130 A1 * | 6/2008 | Chan .............. A61B 17/8605 606/280 |
| 2008/0177311 A1 | 7/2008 | Winslow et al. |
| 2008/0183217 A1 | 7/2008 | Glaser |
| 2008/0208263 A1 | 8/2008 | Butler et al. |
| 2008/0228230 A1 | 9/2008 | Ferree |
| 2009/0018557 A1 | 1/2009 | Pisharodi |
| 2009/0076516 A1 * | 3/2009 | Lowry .............. A61B 17/02 606/90 |
| 2009/0076553 A1 | 3/2009 | Wolter |
| 2009/0163920 A1 | 6/2009 | Hochschuler et al. |
| 2009/0163960 A1 | 6/2009 | Binder et al. |
| 2009/0192549 A1 | 7/2009 | Sanders et al. |
| 2009/0228010 A1 * | 9/2009 | Gonzalez-Hernandez ................. A61B 17/8052 606/70 |
| 2009/0248082 A1 | 10/2009 | Crook et al. |
| 2009/0281543 A1 | 11/2009 | Orbay et al. |
| 2009/0287258 A1 | 11/2009 | Vannemreddy |
| 2009/0306667 A1 | 12/2009 | Lee et al. |
| 2010/0070034 A1 | 3/2010 | Durward et al. |
| 2010/0082067 A1 | 4/2010 | Kondrashov |
| 2010/0131013 A1 | 5/2010 | Ralph et al. |
| 2010/0137919 A1 | 6/2010 | Wolter |
| 2010/0145386 A1 | 6/2010 | Greenhalgh et al. |
| 2010/0193566 A1 | 8/2010 | Scheib et al. |
| 2010/0211109 A1 | 8/2010 | Doerr |
| 2011/0004252 A1 * | 1/2011 | Velikov .............. A61B 17/8061 606/280 |
| 2011/0015681 A1 * | 1/2011 | Elsbury .............. A61B 17/7059 606/281 |
| 2011/0137314 A1 * | 6/2011 | Kuster .............. A61B 17/74 606/70 |
| 2011/0166573 A1 * | 7/2011 | Wenk .............. A61B 17/80 606/71 |
| 2011/0202092 A1 | 8/2011 | Frigg et al. |
| 2011/0230971 A1 | 9/2011 | Donner et al. |
| 2011/0295325 A1 | 12/2011 | Wagner et al. |
| 2012/0016365 A1 | 1/2012 | Freid et al. |
| 2012/0022600 A1 | 1/2012 | Overes et al. |
| 2012/0283776 A1 | 11/2012 | Mishra |
| 2013/0053886 A1 | 2/2013 | Hawkins et al. |
| 2013/0090688 A1 * | 4/2013 | Montello .......... A61B 17/7044 606/246 |
| 2013/0123923 A1 | 5/2013 | Pavlov et al. |
| 2014/0142637 A1 | 5/2014 | Robinson |
| 2014/0207191 A1 | 7/2014 | Kornel |
| 2014/0276807 A1 | 9/2014 | Lovell |
| 2014/0277141 A1 | 9/2014 | Baynham |
| 2014/0277142 A1 | 9/2014 | Blain et al. |
| 2015/0012039 A1 | 1/2015 | Montello et al. |
| 2015/0157373 A1 * | 6/2015 | Wolf .............. A61B 17/8057 606/280 |
| 2015/0173746 A1 | 6/2015 | Baxter, III et al. |

(56) References Cited

U.S. PATENT DOCUMENTS

| | | | |
|---|---|---|---|
| 2015/0190175 A1 | 7/2015 | Oldakowski et al. | |
| 2015/0209089 A1 | 7/2015 | Chataigner et al. | |
| 2015/0215259 A1 | 7/2015 | Pellicer et al. | |
| 2015/0265319 A1 | 9/2015 | Ferree et al. | |
| 2015/0272573 A1 | 10/2015 | Euteneuer et al. | |
| 2015/0297229 A1 | 10/2015 | Schellin et al. | |
| 2015/0297230 A1 | 10/2015 | Schellin et al. | |
| 2015/0297231 A1 | 10/2015 | Huitema et al. | |
| 2015/0297233 A1 | 10/2015 | Huitema et al. | |
| 2015/0297273 A1* | 10/2015 | Harris | A61B 17/80 606/280 |
| 2016/0135851 A1 | 5/2016 | Woodworth et al. | |
| 2016/0354122 A1 | 12/2016 | Montello et al. | |
| 2017/0215931 A1* | 8/2017 | Cremer | A61B 17/8052 |
| 2017/0311990 A1 | 11/2017 | Hirschl et al. | |
| 2018/0140335 A1 | 5/2018 | Hawkins et al. | |
| 2018/0168811 A1* | 6/2018 | Ranganathan | A61F 2/28 |
| 2018/0185075 A1* | 7/2018 | She | A61B 17/8071 |
| 2018/0221067 A1* | 8/2018 | Toro Restrepo | A61F 2/28 |
| 2018/0256221 A1* | 9/2018 | Koay | A61B 17/8061 |
| 2018/0344362 A1 | 12/2018 | Montello et al. | |
| 2019/0046250 A1* | 2/2019 | Sylvestre | A61F 2/36 |
| 2019/0160966 A1 | 5/2019 | Jung et al. | |
| 2020/0179061 A1* | 6/2020 | Richter | A61B 17/7059 |

FOREIGN PATENT DOCUMENTS

| | | |
|---|---|---|
| CN | 201710448 U | 1/2011 |
| CN | 102247207 A | 11/2011 |
| CN | 105377166 A | 3/2016 |
| DE | 4343117 A1 | 6/1995 |
| DE | 19858889 A1 | 6/2000 |
| DE | 10140442 A1 | 3/2003 |
| DE | 102006060933 A1 | 7/2008 |
| EP | 1143867 B1 | 7/2002 |
| EP | 1211994 B1 | 4/2005 |
| EP | 1211993 B1 | 10/2005 |
| EP | 2120754 A1 | 11/2009 |
| EP | 2394587 B1 | 7/2015 |
| EP | 2713897 B1 | 8/2015 |
| EP | 3228269 A1 | 10/2017 |
| FR | 2386301 A1 | 11/1978 |
| FR | 2531855 A1 | 2/1984 |
| GB | 1579575 A | 11/1980 |
| JP | 2008206143 A | 9/2008 |
| JP | 2009511918 A | 3/2009 |
| JP | 2010536427 A | 12/2010 |
| JP | 2017205485 A | 11/2017 |
| RU | 2196535 C2 | 1/2003 |
| RU | 2234878 C2 | 8/2004 |
| UZ | 292 U | 6/2007 |
| WO | 95/10239 A1 | 4/1995 |
| WO | 95/16403 A1 | 6/1995 |
| WO | 1999/38448 A1 | 8/1999 |
| WO | 2001/19264 A2 | 3/2001 |
| WO | 2001/19268 A1 | 3/2001 |
| WO | 2005018472 A1 | 3/2005 |
| WO | 2007/044954 A2 | 4/2007 |
| WO | 2008/077491 A1 | 7/2008 |
| WO | 2009/023666 A2 | 2/2009 |
| WO | 2011/003494 A1 | 1/2011 |
| WO | 2012/135860 A2 | 10/2012 |

OTHER PUBLICATIONS

U.S. Appl. No. 14/491,769, filed Sep. 19, 2014, Posterior Vertebral Plating System.
U.S. Appl. No. 15/238,383, filed Aug. 16, 2016, Posterior Vertebral Plating System.
U.S. Appl. No. 16/055,909, filed Aug. 6, 2018, Posterior Vertebral Plating System.
[No Author Listed] Insight Retractor Surgical Technique Guide, DePuy Synthes, 2012, 32 pages.
[No Author Listed] Insight Tubes Surgical Technique Guide, DePuy Synthes, 2017, 28 pages.
Decision on Grant Patent for Invention (RU 2013148808); dated Oct. 27, 2016.
Extended European Search Report for European Patent Application No. 15162416.0 dated Aug. 14, 2015.
Extended European Search Report for European Patent Application No. 18160551.0, dated Jun. 28, 2018.
Extended European Search Report for European Patent Application No. 17168305.5 dated Sep. 7, 2017.
First Office Action (Chinese Patent Application No. 201610825793. X); dated Jun. 27, 2018.
International Search Report and Written Opinion for Application No. PCT/US2012/031901, dated Jan. 17, 2013.
Notification of Reasons for Refusal for Japanese Patent Application No. 2014-502700; dated Feb. 9, 2016.
Notification of Reasons for Refusal for Japanese Patent Application No. 2016-244158; dated Sep. 5, 2017.
Sharan, Ashwini D. et al., "MIS Posterior Cervical Spine Surgery: Five-Level Fusion through a Novel Cervical Tube," JHN Journal (2011) 6:2, pp. 2-4.

* cited by examiner

SURGICAL PLATING SYSTEMS, DEVICES, AND RELATED METHODS

FIELD

Surgical plating systems, devices, and related methods are disclosed herein, e.g., for stabilizing and immobilizing portions of body for surgical procedures, e.g., spinal surgery.

BACKGROUND

The human spine includes vertebrae and joints that work together to protect the spinal cord from injury during motion and activity. The spinal cord generally includes nerve elements that travel from the brain that allow the brain to command the other portions of the body to respond in a particular fashion. Because the spine is routinely subject to high loads and strain, especially during movement, and the proximity to vital bodily structures that can easily be damaged during implantation or surgery, medical professionals seek to utilize implants that will secure the necessary structures with minimal risk of unwanted migration after implantation. These implants aim to stabilize the spine and its surrounding areas to allow the body sufficient time to heal and utilize the body's own healing techniques to repair the injury.

Existing implants and methods for immobilizing and correcting spinal problems have several shortcomings. After implants are inserted into the spine, a variety of factors can contribute to incomplete healing, which can result in patient complications or even further damage. For example, some approaches to spinal corrective surgeries that insert implants into the body utilize full open incisions that involve tissue and muscle stripping laterally to expose the lateral masses to allow the implant to be secured thereto. Such a technique can be very invasive and traumatic to the patient, as well as greatly increase healing time. Further, due to the forces experienced by the spine, implants that are secured thereto by screws have a risk for screw pull-out, which occurs when the cylindrical portion of the bone which surrounds the screw fails. As a result, implant migration can occur because often implants are secured to bony structures using only a single screw due to the proximity of neighboring structures, such as lateral masses and laminae, which may further slow healing time or require corrective surgery to repair.

Accordingly, it is desirable to provide devices and methods that can be used to stabilize and immobilize bony structures for surgery while minimizing the risks of failure at the implantation site.

SUMMARY

Surgical plating systems, devices, and related methods are disclosed herein, e.g., for stabilizing and immobilizing portions of body for surgical procedures, e.g., spinal surgery. In one aspect, a vertebral plating system is provided that can include a plate having an upper surface, a lower surface, and a plurality of holes that extend from the upper surface to the lower surface, the plate being configured to extend along at least one lateral mass of each of adjacent vertebral levels such that two or more of the plurality of holes define a plurality of fixation points at each lateral mass of the adjacent vertebral levels and a plurality of attachment members configured to be inserted through the plurality of holes in the plate and into the lateral masses of each of the vertebral levels to fix the plate to the vertebral levels. A central longitudinal axis of the plate can pass through at least a portion of each of the plurality of holes and the plate can be formed of a plurality of segments, with each segment including one hole from each of the longitudinal rows of holes.

The devices and methods described herein can have a number of additional features and/or variations, all of which are within the scope of the present disclosure. In some embodiments, for example, the attachment members can include a variable angle locking feature. The variable angle locking feature can range from a 5 degree cone of angulation to a 20 degree cone of angulation. And in some embodiments, the attachment members can engage the plate at a selected angle relative to a central axis of each of the plurality of holes. Further, in some embodiments, the attachment members can include bilaterally angled screws. Still further, in some embodiments, the attachment members can include any one of a trauma screw, an arch screw, or a spine screw.

In certain embodiments, the holes of the system can include a plurality of threaded columns separated by non-threaded recesses. And in some embodiments, one or more of the holes can be threaded. Further, in some embodiments, the threads of one of at least one of the holes can be positioned adjacent to the space to increase the strength of the plate. And in some embodiments, a space can be formed between a hole from the first longitudinal row of holes and an adjacent hole from the second longitudinal row of holes. Further, in some embodiments, the holes can be perpendicular to the central longitudinal axis of the plate. Still further, in some embodiments, the holes can be angled at an angle of approximately 10 to 30 degrees of lateral outward angulation with respect to the plate. And in some embodiments, one or more of the first and second sets of holes can be angled in at least one of a direction that is parallel to the central longitudinal axis of the plate and in a direction that is perpendicular to the central longitudinal axis of the plate.

In certain embodiments, the plate can include a contoured surface, the contoured surface forming a node around each hole of the plurality of holes. And in some embodiments, an angle between adjacent holes in each segment can range from about 30 degrees to about 60 degrees relative to the central longitudinal axis of the plate. Further, in some embodiments, a distance between recesses formed on opposite sides of the bone plate can range from about 5 millimeters to about 6 millimeters and a distance between nodes on opposite sides of the bone plate can range from about 8 millimeters to about 10 millimeters. And in some embodiments, a distance measured between centers of a pair of laterally adjacent holes of the plurality of holes can range from about 2 millimeters to about 5 millimeters.

In some embodiments, the vertebral plating system can include an inserter tool that is configured to implant the plate in the lateral mass. And in some embodiments, the system can include an access tube defining a channel therein, the access tube being configured to receive the bone plate and the attachment members therethrough. Further, in some embodiments, the access tube can include a cut-out formed on a distal end of the access tube.

In certain embodiments, the system can include a mesh material extending from one of the upper surface and the lower surface. And in some embodiments, the mesh material can define rhombal-shaped openings therein. Further, in some embodiments, the mesh material can form a base of one or more of the first and second plates.

In another aspect, a surgical method is provided that can include making an incision on a posterior side of a spinal cord of a patient, inserting an implant into the incision, in which the implant includes a first plate having an upper surface, a lower surface, and a plurality of holes that extend from the upper surface to the lower surface, the plate being configured to extend along adjacent vertebral levels such that two or more of the plurality of holes define a plurality of fixation points at each of the adjacent vertebral levels, a second plate having an upper surface, a lower surface, and a plurality of holes that extend from the upper surface to the lower surface, the plate being configured to extend along adjacent vertebral levels such that two or more of the plurality of holes define a plurality of fixation points at each of the adjacent vertebral levels, and a mesh that extends between the first and second plates. The method can further include positioning the implant within the incision such that the first and second plates are located on opposite sides of the spinal cord, and inserting one or more of a plurality of attachment members through the plurality of holes in the first and second plates to secure the implant at the plurality of fixation points to each of the vertebral levels.

As with the above-described aspect, a number of additional features and/or variations can be included, all of which are within the scope of the present disclosure. In some embodiments, for example, a distance measured between centers of a pair of laterally adjacent holes of the plurality of holes can range from about 2 millimeters to about 5 millimeters. And in some embodiments, the method can include inserting one or more of a plurality of attachment members through a plurality of holes in the mesh to secure the mesh at one or more vertebral levels. Further, in some embodiments, the mesh can include one or more of titanium, titanium alloys, magnesium, and hydroxyapatite. Still further, in some embodiments, the mesh can be coupled to at least one of the first and second plates. And in some embodiments, the method can include additively manufacturing one or more of the mesh and the first and second bone plates.

In certain embodiments, the adjacent vertebral levels can be located in the cervical region of the spine. And in some embodiments, the method can include removing one or more of the lamina and the spinous process prior to inserting the implant.

In another aspect, a surgical implant is provided that can include a first plate having an upper surface, a lower surface, and a plurality of holes that extend from the upper surface to the lower surface, the plate being configured to extend along adjacent vertebral levels such that two or more of the plurality of holes define a plurality of fixation points at each of the adjacent vertebral levels, a second plate having an upper surface, a lower surface, and a plurality of holes that extend from the upper surface to the lower surface, the plate being configured to extend along adjacent vertebral levels such that two or more of the plurality of holes define a plurality of fixation points at each of the adjacent vertebral levels, and a connecting material that extends between the first and second plates.

As with the above-described aspect, a number of additional features and/or variations can be included, all of which are within the scope of the present disclosure. In some embodiments, for example, the plurality of holes in the first and second plates can be arranged in two longitudinal rows such that the holes of a first longitudinal row of holes are offset with respect to a second longitudinal row of holes, with each of the longitudinal rows having a common central axis, a central longitudinal axis of the plate passes through at least a portion of each of the plurality of holes, and the plate is formed of a plurality of segments, each segment including one hole from each of the longitudinal rows of holes. And in some embodiments, one or more of the first and second plates can include conical threads.

In certain embodiments, the implant can include an adhesion preventive coating applied to one or more of a tissue-engaging surface of the first and second plates and the mesh. And in some embodiments, the connecting material can be any one of a mesh or a tab. Further, in some embodiments, the mesh can include a pattern having one or more openings extending along a length thereof. And in some embodiments, the mesh can be integrally formed with one or more of the first and second plates. Still further, in some embodiments the mesh can be coupled to at least one of the first and second plates. And in some embodiments, the mesh can include one or more of titanium, titanium alloys, magnesium, and hydroxyapatite. Further, in some embodiments, a first end of the mesh can be coupled to one of the first and second plates and a second, opposite end of the mesh is not coupled to one of the first and second plates.

In certain embodiments, the tab can connect the first and second plates. And in some embodiments, the tab can be configured to extend transversely with respect to a central longitudinal axis of the plate. Further, in some embodiments, the tab can include one or more wings extending therefrom, the wing being configured to bend to support coupling the tab to an anatomical structure.

In another aspect, a surgical method is provided that includes making an incision along upper spinous processes of a spinal cord of a patient, attaching a plate to one or more of the upper spinous processes, the plate having an upper surface, a lower surface, and a plurality of holes that extend from the upper surface to the lower surface, the plate being configured to extend along adjacent upper spinous processes such that two or more of the plurality of holes define a plurality of fixation points at each of the upper spinous processes, and inserting one or more of a plurality of attachment members through the plurality of holes in the plate to secure the plate at multiple fixation points to the upper spinous processes. A width of the incision according to this method can be less than or equal to a width of one or more of the upper spinous processes to which the plate is secured.

As with the above-described aspect, a number of additional features and/or variations can be included, all of which are within the scope of the present disclosure. In some embodiments, for example, the method can include an access tube to introduce the bone plate through the incision. And in some embodiments, using the access tube can include passing the bone plate through the access tube such that the bone plate is disposed within the access tube, and angling the access tube such that a distal-most end of the bone plate extends radially beyond the walls of the access tube while the bone plate is disposed therein.

In certain embodiments, the method can include shaving one or more portions of the upper spinous processes to provide a flat surface for attaching the plate thereto. And in some embodiments, a ratio of the width of the incision to a width of the upper spinous process can be approximately 1:2.0. Further, in some embodiments, a ratio of the width of the incision to a width of the plate can be 1:1.

In another aspect, a surgical system is provided that can include a plate having an upper surface, a lower surface, and a plurality of holes that extend from the upper surface to the lower surface, the plate being configured to extend along adjacent vertebral levels such that two or more of the plurality of holes define a plurality of fixation points at each of the adjacent vertebral levels, and a plurality of attachment members configured to be inserted through the plurality of holes in the plate and into each of the vertebral levels to fix the plate to the vertebral levels. The plurality of holes in the system can be arranged in two longitudinal rows such that the holes of a first longitudinal row of holes are offset with respect to a second longitudinal row of holes, with each of the longitudinal rows having a common central axis, and a central longitudinal axis of each hole in the first longitudinal row of holes is angled: (1) with respect to a central longitudinal axis of an adjacent hole in the second longitudinal row of holes; and (2) to a central longitudinal axis of the plate such that the attachment members inserted through the holes in the first longitudinal row are configured to be angled with respect to the attachment members inserted through the holes in the second longitudinal row and one of the upper and lower surfaces of the plate.

As with the above-described aspect, a number of additional features and/or variations can be included, all of which are within the scope of the present disclosure. In some embodiments, for example, the method can include an access tube configured to allow one or more of the plate and the plurality of attachment members to pass therethrough. And in some embodiments, the access tube can include a cut-out formed on a distal end of the access tube.

In certain embodiments, the holes of a first longitudinal row of holes can be offset in a direction transverse to the central longitudinal axis of the plate. And in some embodiments, the holes can be angled at an angle of approximately 10 to 30 degrees of lateral outward angulation with respect to the plate. Further, in some embodiments, a distance between recesses formed on opposite sides of the bone plate can range from about 5 millimeters to about 6 millimeters and a distance between nodes on opposite sides of the bone plate can range from about 8 millimeters to about 10 millimeters. In some embodiments, a distance measured between centers of a pair of laterally adjacent holes of the plurality of holes can range from about 2 millimeters to about 5 millimeters. Further in some embodiments, one or more holes in the first longitudinal row of holes can be angled from approximately 10 degrees to approximately 30 degrees cranially in the sagittal plane and laterally in the transverse plane. Still further, in some embodiments, one or more holes in the second longitudinal row of holes is angled from approximately 0 degrees to approximately 10 degrees cranially in the sagittal plane and laterally in the transverse plane.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The following detailed description is provided with the accompanying drawings, in which.

DETAILED DESCRIPTION

Surgical plating systems, devices, and related methods are disclosed herein, e.g., for stabilizing and immobilizing portions of body for surgical procedures, e.g., spinal surgery. An exemplary plating system can include a bone plate having one or more holes therein. The bone plate can have a narrow profile which can allow the bone plate to be used in minimally invasive surgeries (MIS) to speed up patient recovery time. The bone plate can be partitioned into segments that allow the bone plate to be fixed at multiple points to single structure of a patient. For example, each hole is configured to receive an attachment member for coupling the bone plate to a bony structure, e.g., lateral masses, laminae, and so forth, in a body of a patient. In some embodiments, the holes can receive attachment members at various trajectories and angles to increase resistance to back-out from the bony structures. The instantly disclosed plating systems can include a mesh construct and/or additional locking features for increased coupling to the bony structures and preventing unwanted migration of the plating system. In some embodiments, the plating system can be introduced into the patient via an access tube to further limit the invasiveness of the procedure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Plating System

Figure 1:
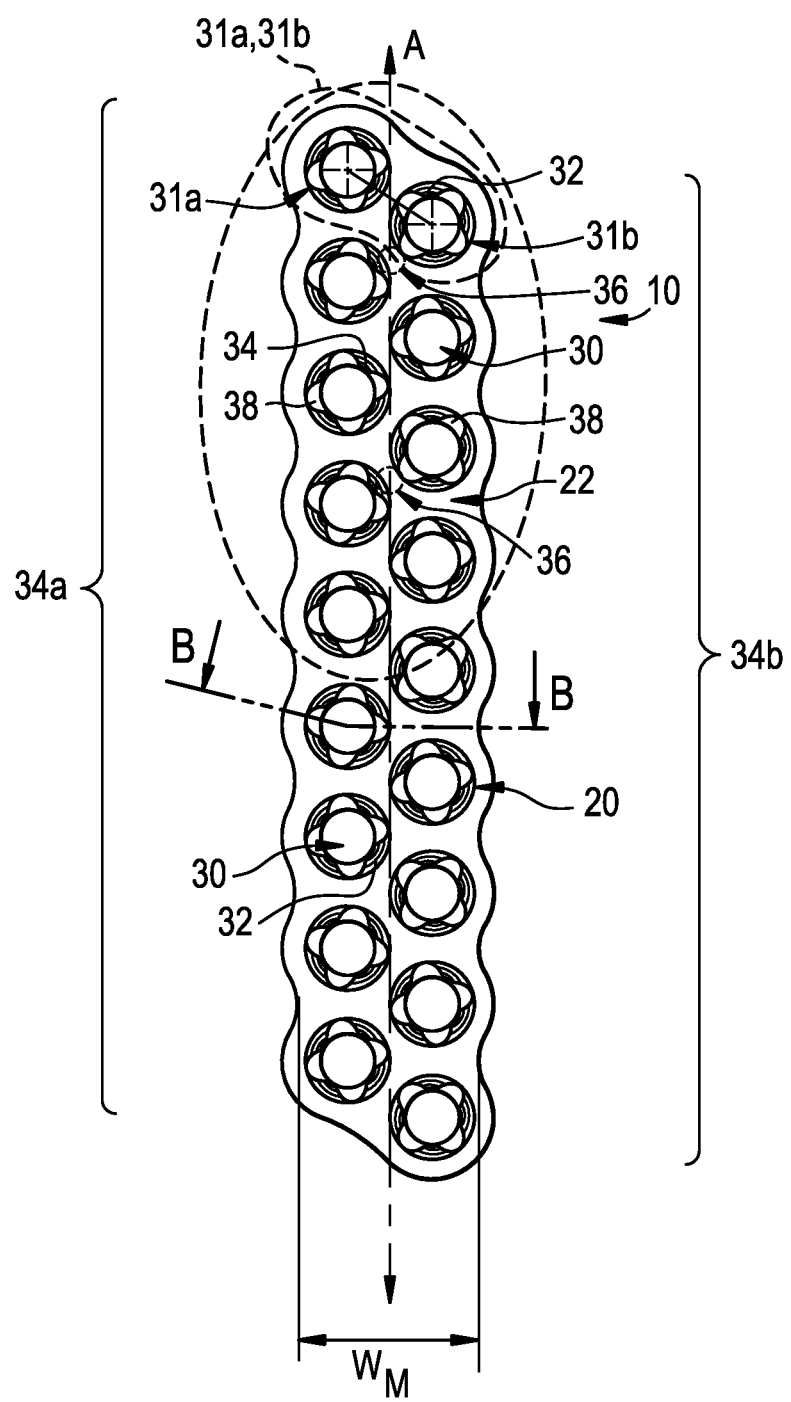
FIG. 1 is a top view of a bone plate of a prior art plating system.

FIG. 1 illustrates a prior art plating system 10. The plating system 10 can include a bone plate 20 having an upper surface 22, a lower surface (not shown), and a plurality of holes 30 which extend from the upper surface to the lower surface. The holes 30 are dimensioned and arranged relative to one another so that more than one of the holes 30 is positionable or alignable over the posterior boney structures, such as the lateral mass or lamina, of each vertebra to define a plurality of fixation points per vertebra. Each hole 30 can include threads 32 to receive attachment members therein to fix the bone plate to the boney structures.

The holes 30 are arranged in two longitudinal rows or sets 34a, 34b of holes 30 along the length of the bone plate 20 with the holes 30 of a first set of holes 34a being staggered relative to the holes 30 of a second 34b set of holes 30. Each of the holes 30 can be arranged where each laterally adjacent pair of holes 31a, 31b are spaced substantially a first distance, and each pair of longitudinally adjacent holes are spaced substantially a second distance where the second distance is greater than the first distance and each laterally adjacent pair of holes 31a, 31b are angled relative to one another at approximately 33 degrees relative to a longitudinal axis A of the bone plate 20. As shown, the holes 30, while being staggered, do not overlap with one another along the longitudinal axis A, but are aligned with the longitudinal axis A to minimize a width of the bone plate 30. To offset the relatively narrow width of the bone plate 20 and the inclusion of multiple holes 30 impacting a strength of the bone plate 20 in the spaces 36 between the holes 30, which tend to be narrowest portions of the bone plate 30 and therefore the most prone to deformation, threads 32 of one of the holes intersects a line L extending between the axes of laterally adjacent holes 31a, 31b such that the threads 32 function to provide a thicker area between two laterally adjacent holes 31a, 31b than would exist if the recesses 38 were aligned in lieu of the threads. The thicker area can provide the advantage of increased strength of the bone plate 20. Additional information about the bone plate 20 can be found in U.S. Pat. No. 8,845,697, filed on Apr. 2, 2012, which is hereby incorporated by reference in its entirety.

Surgical Plating Systems, Devices, and Methods

Figure 2:
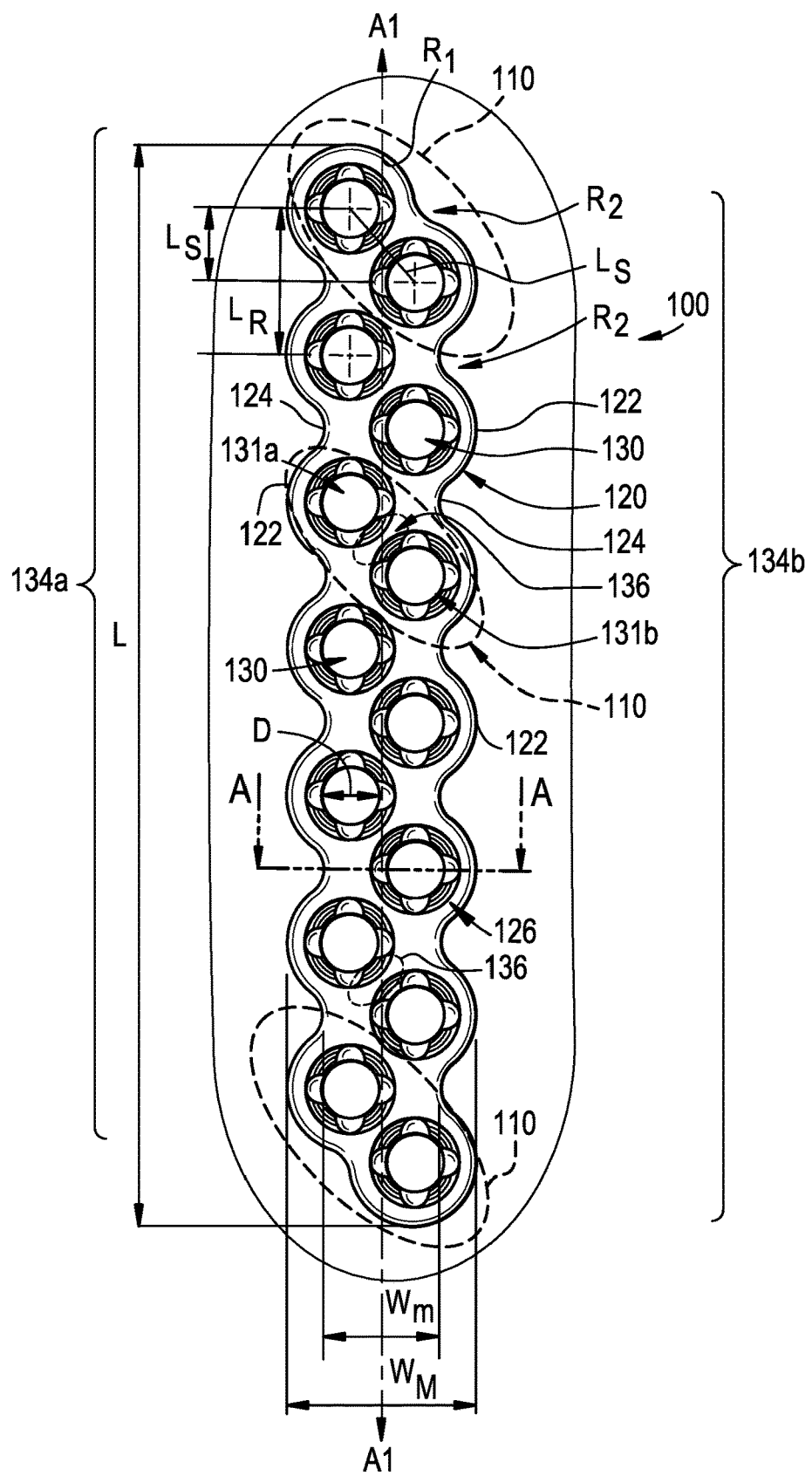
FIG. 2 is a top view of one embodiment of a bone plate of a plating system.

FIG. 2 illustrates an embodiment of a plating system 100 according to the present disclosure that includes a bone plate 120 having a different layout of holes, as discussed further below. The plating system 100 can be used in various regions of the spine, e.g., cervical, lumbar, thoracic, and sacral, or between two regions of the spine to immobilize and stabilize multiple vertebrae and/or other boney structures. This layout can also create a bone plate 120 that has a narrower profile than that of FIG. 1, discussed above, for use in procedures that have greater limitations on size. For example, the bone plate 120 can be used in minimally-invasive surgical procedures to take advantage of the narrower profile of the bone plate when navigating through smaller incisions and smaller spaces between body structures. The narrower profile can also allow the plating system 100 to be introduced into the spine in multiple directions for increased maneuverability within the spine and more secure fixation, as described further below. It will be appreciated that the illustrated plating system 100 is exemplary and that other plating systems having additional or alternative features can be used with the instruments herein. In some embodiments of the plating system 10, the holes 30 are arranged in such a manner that the spaces 36 between laterally adjacent holes 31a, 31b is minimized, as compared to FIG. 1, whereby the opposing pairs of columns of threads 32 generally provide the structure between each laterally adjacent pair of holes 31a, 31b.

The plating system 100 includes a bone plate 120 that is configured to stabilize multiple vertebrae to achieve multi-point fixation at each vertebral level. Multipoint fixation allows for more secure fixation between the plating system and the vertebrae, as compared to conventional screws and rods that offer a single point of fixation at each vertebral level, to prevent slippage of the plating system relative to the vertebrae during or after surgery. This can be helpful for a number of reasons, e.g., certain areas of the spine can be subjected to large loads and stress forces that can cause unwanted migration of implants that are not sufficiently secured thereto.

The dimensions of the bone plate 120 can be varied based on a number of vertebrae to be stabilized. For example, the bone plate 120 can be manufactured such that a length L and/or a width W of the bone plate 120 corresponds to the dimensions of the vertebrae to be secured to the bone plate 120. In some embodiments, a length of the bone plate 120 can be such that it extends over two or more vertebrae to stabilize the vertebrae relative to one another. The bone plate 120 can be manufactured, e.g., welded, machined, three-dimensionally printed, and so forth, to the desired length and/or width. In some embodiments, the bone plate 120 can be adjustable to allow for in-situ expansion and reduction in length and/or width based on the number, size, and/or dimensions of the vertebral levels to be stabilized. For example, the bone plate can include portions configured to facilitate breaking or cutting the bone plate such that, for example, a long plate can be shortened during a procedure based on the particular anatomy of the patient, etc.

The ability to customize the dimensions of the bone plate 120 can facilitate use of the bone plate in minimally invasive surgeries (MIS) and other techniques designed to limit and/or minimize the trauma to the patient. For example, in some embodiments, the bone plate can have an overall width in a range of about 6 millimeters to about 10 millimeters, about 7 millimeters to about 9.5 millimeters, about 8 millimeters to about 9.25 millimeters, or about 9 millimeters.

To further minimize the profile of the bone plate 120 while maintaining multipoint fixation at each vertebral level, the width of the bone plate 120 may be varied to eliminate excess material that does not assist with bone plate fixation. For example, the bone plate 120 can be curved or contoured along one side or multiple sides such that the bone plate 120 is configured to have a plurality of nodes 122 which define recesses 124 between each of the nodes 122 to reduce the outer contour of the bone plate 120. As shown, the bone plate 120 may have at least one minor width $W_m$ defined between recesses on opposite sides of the bone plate, and at least one major width $W_M$ defined between nodes on opposite sides of the bone plate. The minor width $W_m$ can range from about 4 millimeters to about 9 millimeters, from about 5 millimeters to about 7 millimeters, from about 5.25 millimeters to about 6 millimeters, or have a value of about 5.5 millimeters, and the major width $W_M$ can range from about 8 millimeters to about 10 millimeters, or be about 9 millimeters. The reduced width portion between each of the nodes 122 provides an area of reduced material for bending of the bone plate 120 as may be required by the spinal anatomy, as well as provides for better visualization of the boney surface below the bone plate 120. The bone plate 120 has a thickness that can range from about 1 millimeter to about 6 millimeters, for example.

In some embodiments, the radii of curvature can also be optimized to eliminate excess material of the bone plate. As shown, the bone plate 120 can include at least one node radius of curvature R1 and at least one recess radius of curvature R2. In some embodiments, the node radius of curvature can range from about 2.5 millimeters to about 3.5 millimeters, from about 2.75 millimeters to about 3.25 millimeters, or have a value of about 3 millimeters, and the recess radius of curvature can range from about 1 millimeters to about 1.5 millimeters, from about 1.25 millimeters to about 1.35 millimeters, or have a value of about 1.3 millimeters.

Figure 5:
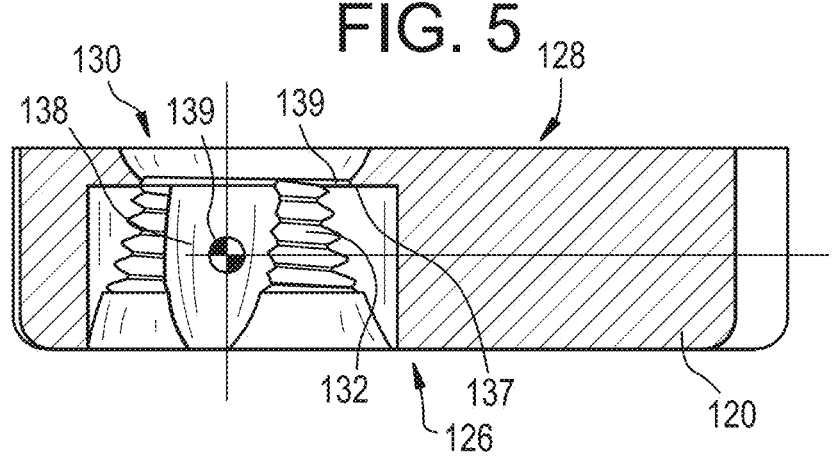
FIG. 5 is a cross-sectional view of a hole of the bone plate of FIG. 2.

The bone plate 120 can include an upper surface 126 and a lower surface 128 (see FIG. 5). In some embodiments, the bone plate 120 can include one or more rounded edges to reduce irritation of surrounding tissue. The rounded edges can be located along the sides of the bone plate 120 and can extend around the perimeter of the bone plate 120. The rounded edge reduces the amount of trauma or irritation that would be experienced by the surrounding soft tissue. In some embodiments, the lower surface 128 of the bone plate 120 can conform to the contour of the boney surfaces on which the bone plate is disposed to prevent unwanted migration that can be caused by uneven contact points between the bone plate and the bodies. In other embodiments, the lower surface 128 can include any of a variety of surface features formed thereon to prevent unwanted migration, e.g., protruding features such as teeth, a roughened surface texture, etc.

The bone plate 120 can include one or more holes 130 which extend through the bone plate 120 from the upper surface 126 through the lower surface 128. The holes 130 can be dimensioned and arranged relative to one another so that more than one of the holes 130 is positionable or alignable over the posterior boney structures, such as the lateral mass or lamina, of each vertebra to define a plurality of fixation points per vertebra. The holes 130 can include threads 132 throughout an inner surface of the holes configured to receive threaded attachment members therein. In some embodiments, the threads 132 can be interrupted by recesses 138 (see FIGS. 3 and 4) to enable attachment members to be threaded into the holes 130 at various angles, as discussed further below.

The holes 130 can be arranged in a variety of ways to provide multiple points of fixation while maintaining the structural strength and rigidity of the bone plate 120. For example, FIG. 2 illustrates one exemplary embodiment of a hole pattern where the holes 130 can divide the bone plate into segments 110 that correspond with one of the nodes. For example, the bone plate can be formed of segments 110 that include two holes per segment, as shown, though, in some embodiments, one or three or more holes 130 are formed in each segment. Each segment 110 can be positioned over a single vertebra to define a plurality of fixation points per vertebra. As shown in FIG. 2, each side of the bone plate 130 can include seven nodes 122, with each node defining a segment 110. In such a configuration, the bone plate can couple to multiple vertebral levels, e.g., four, each having one or multiple segments coupled thereto. With regards to vertebrae of the spine, it will be appreciated that the bone plate 120 can couple to any number of vertebrae depending upon the length of the bone plate 120 and the number and arrangement of attachment members. In some embodiments, the positioning of the nodes 122, the recesses 124, and the holes 130 of the bone plate 120 can be customized based on the dimensions of the boney structures to which the bone plate is coupled.

As shown, the holes 130 are arranged in groups of two holes per segment 110, with the holes 130 in each segment being angled with respect to one another. The angle between the holes 130 in each segment 110 can be uniform in each segment or vary between segments. The holes 130 can be angled toward and/or away from one another along the width direction (medially-laterally), toward and/or away from one another along the length direction (cranially-caudally) or in one or more combinations of direction thereof. For example, as shown in FIG. 2, the angle between adjacent holes in each segment can range from about 30 degrees to about 60 degrees, about 40 degrees, to about 55 degrees, or have a value of about 50 degrees. In some embodiments, the angle of the holes 130 can vary along the length of the plate 120 such that the angle in the holes 130 is non-uniform across the length of the plate 120.

As shown, the holes 130 can be arranged in at least two longitudinal rows or sets 134a, 134b of holes 130 along the length of the bone plate 120 with the holes 130 of a first set of holes 134a being staggered and nested relative to a second set 134b of holes 130 of the other longitudinal row of holes 130. The staggered orientation between each set of holes allows the bone plate to have a narrower profile and a narrower width to facilitate implantation during MIS procedures. To achieve the staggered orientation, one or more holes 130 of the first and second sets of holes 134a, 134b can be arranged such that a portion of the holes 130 can cross a central longitudinal axis A1 of the bone plate 130 so as to result in a significant overlap of laterally adjacent holes 131a, 131b along a longitudinal axis of the bone plate 120. In some embodiments, the overlap of laterally adjacent holes 131a, 131b can be up to, and including, about 50% of a diameter D of the holes 130 so as to permit adjacent holes 130 in the first set of holes 134a and the second set of holes 134b to remain spaced to align with the lateral mass of the vertebra while minimizing the width $W_M$ of the bone plate 120.

Despite the staggered orientation of the holes 130 of the bone plate 120, the holes 130 include one or more spaces 136 therebetween. As shown, the spaces 136 can be defined between the outermost points of the holes 136. Due to the narrow width of the bone plate 120 and the inclusion of multiple holes, a strength of the bone plate 120 can be compromised along the narrowest portions of the plate 120, which can occur between laterally adjacent holes. To increase the strength of the bone plate 120, the plate can maintain a distance between the holes 130 to add thickness to the points along the bone plate 120 that can otherwise fail due to the absence of material when the holes 130 are positioned too close to one another. In some embodiments, the strength of the bone plate 120 can further be increased by positioning at least one of the columns of threads 132 of one of the holes 130 of a pair of laterally adjacent holes adjacent to the space 136. The columns of threads 132 function to provide a thicker area between two laterally adjacent holes than would exist if the recesses 138 were aligned, thereby further strengthening the bone plate. As shown in FIG. 2, in some embodiments, both holes can be positioned such that the column of threads 132 of both holes 130 are adjacent to the spaces 136 throughout the length L of the bone plate.

In some embodiments, the number of segments 110 can be increased or decreased to vary the overall length of the bone plate 120. While the segments of the bone plate 120 of FIG. 2 are substantially linear, in some embodiments, the segments 110 can be arranged in square, rectangular, and/or triangular patterns. Each pair of holes 130 in each segment 110 may be arranged where each laterally adjacent pair of holes in an adjacent segment 110 is spaced substantially an equal distance from one another, though, in some embodiments, the distance between laterally adjacent pairs of holes in an adjacent segment 110 can vary. The distance between corresponding holes in adjacent segments can vary based on the angle between the holes, the length of the plate, and the desired length of each segment, among other factors. Distance $L_S$, measured between the centers of a pair of laterally adjacent holes in a segment can range from about 2 millimeters to about 5 millimeters, from about 3 millimeters to about 4 millimeters, or have a value of about 3.5 millimeters. Further, as shown, each pair of longitudinally adjacent holes 130 in a set is spaced a greater distance apart than each pair of laterally adjacent holes. For example, a distance $L_R$, measured between the centers of a pair of longitudinally adjacent holes 130 in a set can range from about 4 millimeters to about 10 millimeters, from about 6 millimeters to about 8 millimeters, or have a value of about 7 millimeters.

The holes 130 may be formed entirely perpendicular to the plane of the bone plate 120, or may be offset in a general direction to support angular attachment members therein. Angular attachment members, as discussed further below, can increase the strength of the attachment of the bone plate and minimize the risk of compromising vascular and neural structures. For example, the holes 130 may be laterally outwardly angled, e.g., at an angle of approximately 10 to 30 degrees of lateral outward angulation, as described further below, though in some embodiments, the holes 130 can be angled inwardly, up or down, perpendicular to the plane of the bone plate 120, and so forth. In some embodiments, the holes 130 can include approximately 5 to 15 degrees of medial angulation, in lieu of or in addition to the above lateral outward angulation.

The holes 130 can be configured to receive attachment members therein. As shown, the holes 130 are round so as to receive screws, pins, and similar attachment members therein, though, in some embodiments, the holes can be square, triangular, rectangular, or in the shape of any other polygon known to one skilled in the art, e.g., regular and/or irregular polygons, to receive correspondingly shaped attachment members therein. The diameter D of the holes 130 can vary but, in some embodiments, the diameter D can range from about 2 millimeters to about 3.5 millimeters, from about 2.5 millimeters to about 3 millimeters, from about 2.75 millimeters to about 2.9 millimeters, or have a value of about 2.8 millimeters. Although the bone plate 120 is shown to have uniformly sized holes 130, in some embodiments of the bone plate 120, the diameter D of the holes can vary. Varying the diameter of the holes can allow the bone plate to receive larger and/or stronger attachment members therethrough to further improve coupling of the bone plate to boney structures that may be particularly difficult to stabilize.

Figure 3:
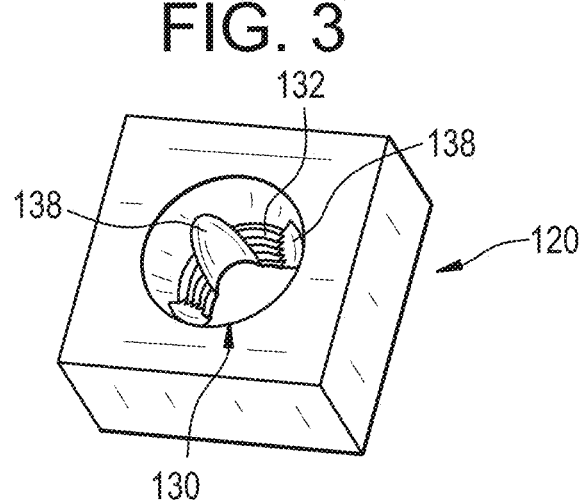
FIG. 3 is a schematic perspective view of one embodiment of the hole of the bone plate of FIG. 2.
Figure 4:
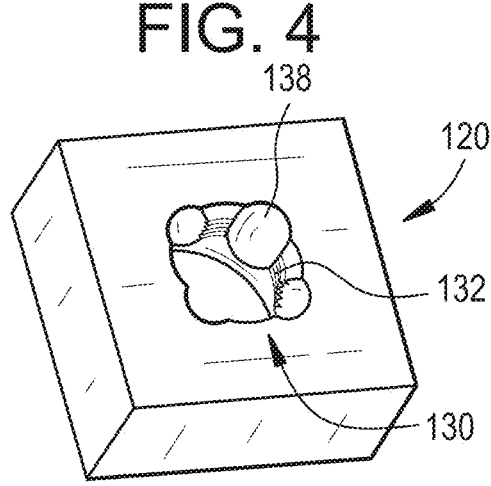
FIG. 4 is a schematic perspective view of another embodiment of the hole of the bone plate of FIG. 2.

The bone plate 120 can include a variety of locking features. For example, one or more holes 130 in the bone plate 120 can include variable angle locking. FIGS. 3-5 illustrate one exemplary embodiment of the structure of the hole 130 having a variable angle locking feature therein. As shown, one or more of the holes of the plurality of holes in the bone plate can include threads 132 to receive correspondingly threaded attachment members. As used herein, the term "attachment member" is intended to refer to any member that may be used to attach a bone plate to a vertebral bone surface, including, but not limited to, screws, clamps, wire, compression screws, locking screws, tacks, pins, nails, studs, rivets, fasteners, or other such devices known to persons having ordinary skill in the art. Those skilled in the art will understand that any thread configuration may be used, or the holes 130 may even be smooth or non-threaded. The threads 132 can receive an attachment member in various forms therethrough. Some non-limiting examples of attachment members can include nails, pins, screws, and so forth. In some embodiments, the holes 130 can receive attachment members such as trauma screws, spine screws, and/or arch screws therein, as discussed below.

The threads 132 in the holes 130 are discussed in greater detail with reference to FIGS. 3-5. As shown, the holes 130 can have a plurality of columns of threads 132 spaced apart to define a plurality of non-threaded recesses 138. The columns of threads 132 are arranged around the inner surface of each of the holes 130 for engaging threads on a head of locking and variable angle locking bone screws. Each of the holes 130 can include four columns of threads, as shown in FIGS. 3 and 4, though, in some embodiments, the number of columns of threads can vary. Conventional locking screws can engage the bone plate 120 coaxially with the central axis of the hole of the bone plate 120, while variable angle locking screws can engage the bone plate 120 at a selected angle within a range of selectable angles relative to the central axis of hole of the bone plate 120. The shape of the recesses can vary based on the attachment members received therein. In some embodiments, the shapes of the recesses can restrict the holes 130 to receive a particular shape and/or type of attachment member therein.

FIG. 5 illustrates the relationship between the columns of threads 132 and the recesses 138 in greater detail. The recesses 138 can be defined between the columns of threads 132 to correspond to a shape of the attachment members received therethrough. As shown, a thread size of the columns of threads 132 can stay constant independent of plate thickness, though, in some embodiments, the thread size can vary. Constant thread size can allow the attachment members to travel through the holes smoothly and without impedance, while providing increased stability between the attachment members and the bone plate to prevent loosening or back-out of the attachment members.

In some embodiments, the holes can include one or more features or increasing the safety of attachment members being threaded therethrough. For example, the holes can include a flange 137 extending between adjacent columns of threads 132 near the lower surface 128 of the bone plate 120 in such a way that the flange 137 functions to obstruct the attachment member 140, such as a variable angle screw, from being driven too deeply into the vertebra and thereby limit the risk of injury to patients. In some embodiment, the flanges 137 are formed coextensively with respect to the lower most thread of the columns of threads 132 so as to engage with threads on a head of the variable angle locking screw when the head is fully driven into the hole 130 and thereby provides an obstruction to the variable angle locking screw. It will be appreciated that the attachment member 140 may alternatively, or in addition to, have a flange element or stop member that contacts a portion of the bone plate 120 to limit the depth or distance which the attachment member 140 may be inserted into the bone. In some embodiments, a size of the threads 132 can stay constant independent of a thickness of the bone plate 120. In such embodiments, the hole 130 includes a larger non-threaded conical portion that extends between the upper surface 126 and the column of threads 132.

Figure 6:
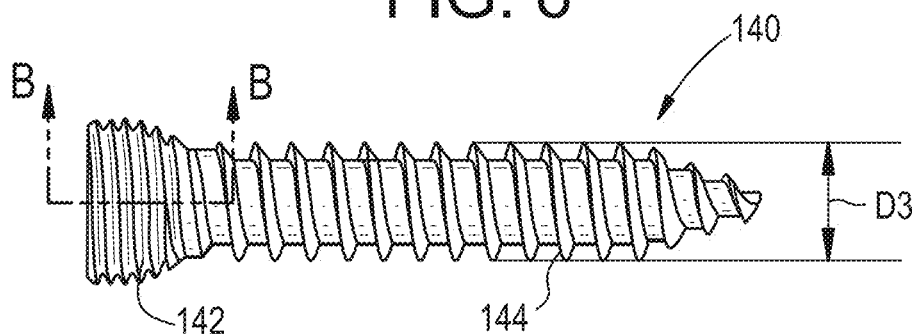
FIG. 6 is a schematic side view of one embodiment of an attachment member used with the bone plate of FIG. 2.
Figure 7:
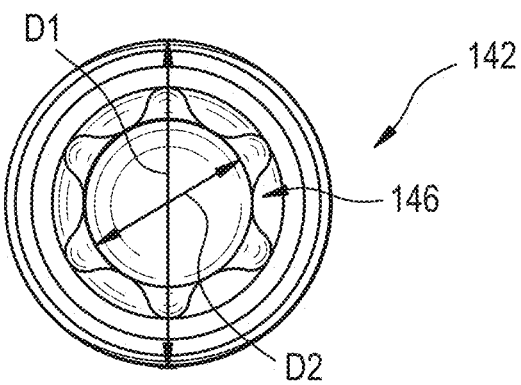
FIG. 7 is a schematic top view of the attachment member of FIG. 6.
Figure 8:
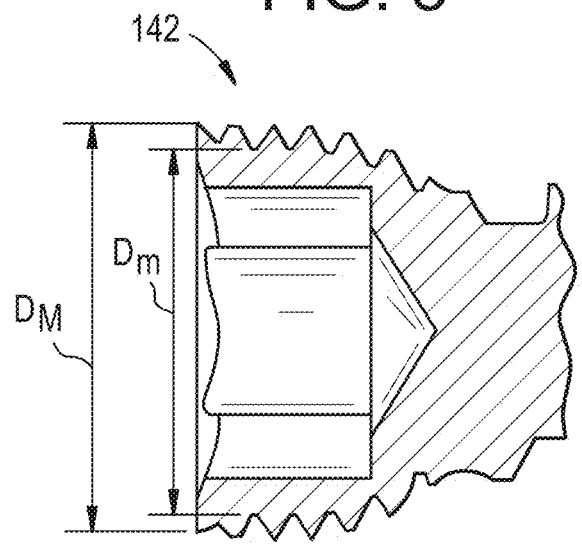
FIG. 8 is a side cross-sectional view of the attachment member of FIG. 6.

FIGS. 6-8 illustrate an exemplary embodiment of an attachment member 140 that can be inserted through the holes of the bone plate. The attachment member 140 can include a threaded head 142 and a body portion 144 that can be used for variable angle locking. As shown, the attachment member 140 can be a screw that has features of a trauma screw and/or an arch screw to allow for easy insertion through the bone plate 140 and into boney structures. For example, the threaded head 142 can be conical while the body portion 144 can be sharp-tipped (e.g., self-tapping) and/or self-drilling. Screws of this type provide for strong grip which allows for secure insertion into lateral masses and other spinal structures.

A proximal portion of the attachment member 140 is shown in greater detail in FIG. 8. The head 142 can be at least partially spherical with threads thereon. The attachment member 140 can have a profile that follows the arc-shaped radius of curvature of the spherical portion of the head 142. Further details on variable angle locking screws are disclosed in U.S. 2008/0140130 to Chan et al., which is hereby incorporated by reference in its entirety. During implantation, the variable angle capability of the variable angle locking screw 140 allows a surgeon to place the variable angle locking screw 140 within the vertebra at any angle within defined angulation limits, thereby providing for greater flexibility than does a fixed angle screw. Variable angle attachment members 140 that are inserted at an angle with respect to the bone plate 120 can increase the stability of the plating system 100 as compared to attachment members that are inserted perpendicular to the bone plate. For example, the variable angle screw can move in a 5 degree cone of angulation, in a 10 degree cone of angulation, in a 15 degree cone of angulation, and/or in a 20 or more degree cone of angulation with respect to a central/nominal axis of the hole 130. In some embodiments, the attachment member 140 can allow for up 10 degrees of variable angle motion before locking to the plate 120.

The threaded head 142 can be sized such that the head can be received and become disposed in the holes 130 of the bone plate 120. For example, the threaded head 142 can include a major diameter $D_M$ that ranges from about 2.75 millimeters to about 4 millimeters, about 3 millimeters to about 4 millimeters, from about 3.25 millimeters to about 3.5 millimeters, or have a value of about 3.35 millimeters, and a minor diameter $D_m$ that ranges from about 2.5 millimeters to about 3.75 millimeters, about 2.75 millimeters to about 3.5 millimeters, from about 3 millimeters to about 3.25 millimeters, or have a value of about 3.15 millimeters. It will be appreciated that the size of the threaded head 142 can be chosen based on the location into which the screw is inserted and/or the diameter of the bone plate 120 being attached.

The threaded head 142 can be sized so as to receive a driver tool therein. The threaded head 142 can include a drive feature 146 formed therein configured to receive the driver tool therein. The driver feature can have a diameter D2 that ranges from about 1.5 millimeters to about 2 millimeters, about 1.6 millimeters to about 1.8 millimeters, or have a value of about 1.7 millimeters. While a threaded headed is shown, in some embodiments, the head can be non-threaded or have threads on only a portion thereof.

The body portion 144 can be sized so as to extend through the hole 130 and become sufficiently disposed in the boney structure to prevent implant migration. For example, the body portion 144 can have a diameter D3 that ranges from about 2 millimeters to about 3 millimeters, about 2.25 millimeters to about 2.75 millimeters, from about 2.3 millimeters to about 2.5 millimeters, or have a value of about 2.4 millimeters. The threads can be spaced out every of an inch. The thread runout can over a quarter of a revolution or less.

Figure 9:
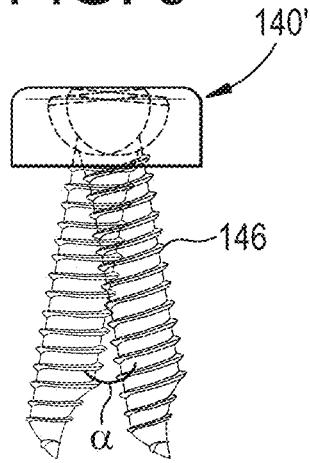
FIG. 9 is a perspective view of one embodiment of bilaterally angled attachment members used with the bone plate of FIG. 2.

FIG. 9 illustrates an alternate embodiment of an attachment member 140' that can be used with the bone plating system 100 disclosed herein. As shown, the attachment member 140' can be bilaterally angled screws that feature variable angle locking. The angle α formed between the bilaterally angled screws can range from about 1 degree to about 30 degrees, from about 3 degrees to about 15 degrees, from about 5 degrees to about 12 degrees, or have a value of about 10 degrees. The screws can have a diameter that ranges from about 2 millimeters to about 3 millimeters, from about 2.2 millimeters to about 2.8 millimeters, from about 2.4 millimeters to about 2.7 millimeters, or other dimensions known to one skilled in the art.

In some embodiments, the attachment members can have a bone thread, e.g., a cortical thread 146, formed thereon. As shown, the cortical thread 146 can circumscribe an entire length of the attachment member 140, though, in some embodiments, a portion of the screw can be non-threaded. Further, in some embodiments, the variable angle locking screws can be self-drilling screws. Self-drilling screws can allow faster screw placement by eliminating the drilling step. For example, the thread could be a double or triple lead thread to allow more rapid insertion of the screws through the bone plate. In some embodiments, the attachment member 140' can allow for up 10 degrees of variable angle motion before locking to the plate 120.

Figure 10A:
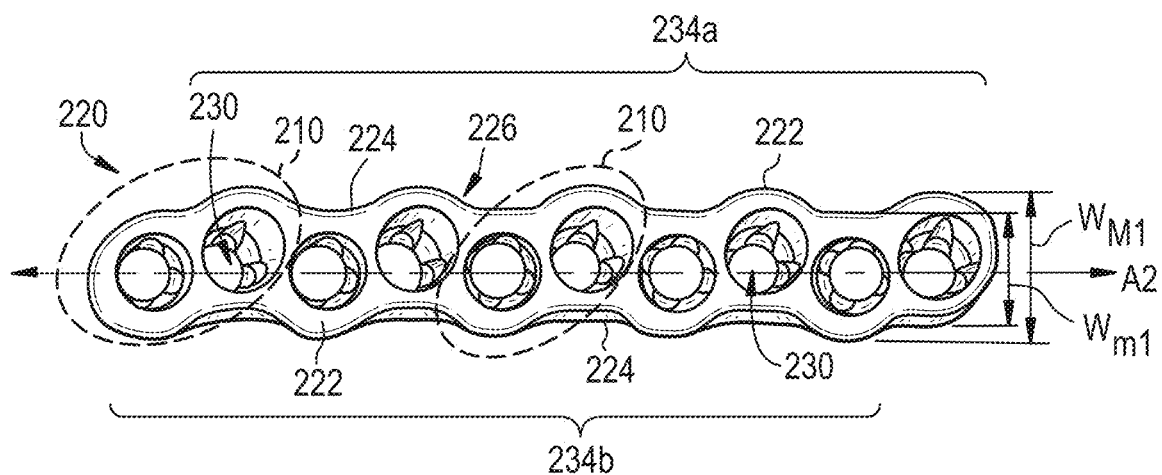
FIG. 10A is perspective top view of one embodiment of a bone plate having bilaterally angled holes.
Figure 10B:
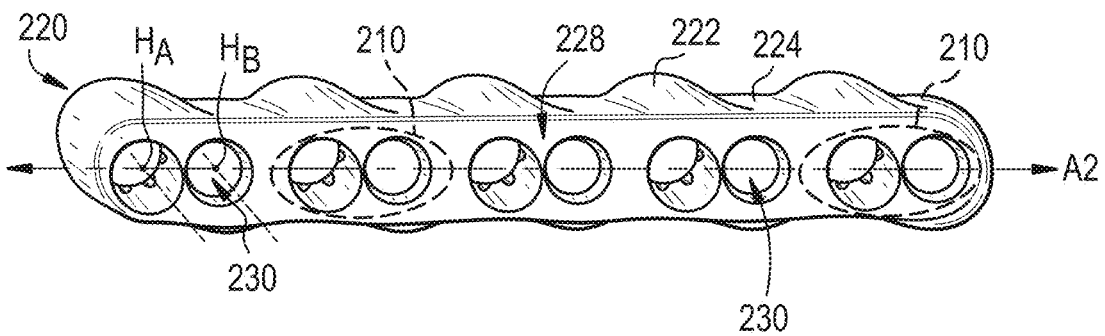
FIG. 10B is a bottom perspective view of the bone plate of FIG. 10A.

FIGS. 10A and 10B illustrate an alternate embodiment of a bone plate 220 that can be used in the bone plating system 100 disclosed herein having a narrower width. As shown, the bone plate 220 can have holes 230 that are staggered with respect to one another but are closer to a central longitudinal axis of the plate as compared to the above-described bone plate 120 to allow the bone plate to have a narrower profile. For example, the bone plate 220 may have at least one minor width $W_{m1}$ defined between recesses on opposite sides of the bone plate and at least one major width $W_{M1}$ defined between nodes on opposite sides of the bone plate. The minor width $W_{m1}$ can range from approximately 5.5 millimeters to approximately 7.5 millimeters, and the major width can range from about 7 millimeters to about 10 millimeters. The reduced width portion between each of nodes 222 provides for recesses 224, or an area of reduced material, for performing minimally invasive procedures and/or providing additional space for placement between bones, as well as provides for better visualization of the boney surface below the bone plate 120. The bone plate 220 has a thickness that can range from about 3 millimeters to about 6 millimeters, for example. The narrower profile can allow the bone plate 220 to be placed through smaller incisions and narrower areas of lateral masses while maintaining multipoint fixation at each vertebral level. This bone plate design can be suitable for patients with smaller bone anatomy, e.g., children or patients with spinal defects, or for less invasive approaches during surgery, e.g., minimally invasive surgeries (MIS), etc.

As shown, the bone plate 220 can include a plurality of segments 210, with each segment having two holes 230 staggered or offset with respect to one another relative to a central longitudinal axis A2 of the bone plate 220. The orientation of the bone plate 220 allows at least two attachment members to be inserted per lateral mass, though three or more attachment members can be inserted per lateral mass in some embodiments. For multipoint fixation to occur in bone plate 220, an attachment member is inserted into each of the holes 230. The staggered orientation of the holes 230 can result in the bone plate 220 having a plurality of rows or sets 234a, 234b of holes 230 disposed along a length of the bone plate. For example, as shown in FIG. 10A, each set 234a, 234b can be offset from the central longitudinal axis A2 of the bone plate 220, with each set having a common longitudinal axis extending therethrough. It will be appreciated that despite the offset from the central longitudinal axis A2 of the bone plate, a portion of one or more holes 230 of each set 234a, 234b can cross the central longitudinal axis A2 to allow the overall bone plate 220 to have a narrower profile.

Each set 234a, 234b can have unique characteristics. For example, the holes 230 in each set 234a, 234b can have a predefined angle to receive one or more attachment members therethrough. The existence of the angled holes in the instantly disclosed bone plate 220 can allow for an increase in the pull-out strength of the attachment members due to a wedging effect. In some embodiments, a hole axis $H_A$ of the holes of the first set 234a can be different from a hole axis $H_B$ of the holes of the second set 234b. The hole axis can extend from a top surface 226 of the bone plate 220 to a bottom surface 228 of the bone plate 220 to receive the attachment members therethrough to attach the bone plate 220 to body structures, e.g., vertebrae.

The hole axis $H_A$ of the first set 234a can be angled in one or more directions to improve attachment of the bone plate 220 to body structures. For example, the hole axis $H_A$ can be angled cranially-caudally in the sagittal plane and laterally-medially in the transverse plane. The hole axis $H_A$ of the first set 234a can be angled approximately 20 degrees cranially and laterally in the sagittal and transverse planes, respectively, though, in some embodiments, the hole axis $H_A$ can range from approximately 10 degrees to approximately 30 degrees. Angled holes can allow a surgeon to insert longer screws into predefined locations along the lateral mass to achieve greater fixation of the bone plate. Longer screws can be used due to Magerl screw trajectory, which is more similar to a traditional lateral mass screw trajectory that is performed in current surgeries with screw and rod systems. By approximating the Magerl trajectory for lateral mass screws, screws or other attachment members disposed in the first set 234a of holes 230 can reduce likelihood of impinging the facet at the caudal level of the construct. In some embodiments, the holes 230 of the bone plate 220 can be set deeper into the bone plate, with a cylindrical lead-in feature to allow for alignment of a drill guide or drill and tap guide or drill, tap and screw guide (DTS guide) with one or more hole axes. The guide can interact with the holes 230 such that the cylindrical lead-in leads and limits angulation of the guide. The guide can interact with more than one of the holes 230 and allows for drilling of more than one hole and/or screw placement without repositioning the drill guide. The DTS guide allows for drilling, tapping, if required, and screw placement through the guide without having to reposition or reattach the guide.

The second set 234b of holes 230 can include an angled hole axis $H_B$ that is angled in one or more of the sagittal and transverse planes (i.e., angled in a direction parallel to the central longitudinal axis A2 of the plate and angled in a direction perpendicular or otherwise transverse to the central longitudinal axis A2 of the plate, respectively). As shown, the hole axis $H_B$ of the second set 234b can be angled approximately 5 degrees cranially and laterally in the sagittal and transverse planes, respectively though, in some embodiments, the hole axis $H_B$ can range from approximately 0 degrees to about 10 degrees, as disclosed further below. While the hole axis $H_B$ of the second set 234b of holes 230 has a smaller angulation of the hole axis than the first set 234a, it will be appreciated that in some embodiments, the hole axis $H_B$ of the second set 234b can have a larger angulation of the hole axis $H_A$ than the first set 234a. The set having smaller angled holes can reduce the likelihood of medial breach of the lateral mass when the plate is aligned with the medial edge of the lateral mass.

In some embodiments, the angulation of the hole axis in the first and second sets 234a, 234b can be the same, while in further embodiments, one or more holes 230 in each set can have a different angulation of the hole axis than the remaining holes in the set. The angulation of the hole axes of the first and second sets 234a, 234b of a single segment 210 is such that attachment members 240 disposed in the first set 234a converge with attachment members 240 disposed in the second set 234b, as described further below. For example, in some embodiments, the holes 230 can be angled cranially in the sagittal plane and/or laterally in the transverse plane. The angle of these holes can be uniform or vary across a length of the sets 234a, 234b. In other embodiments, the angle of one or more the holes 230 can be predefined and/or vary based on underlying anatomy, e.g., the patient's height, weight, and so forth, to which the plate 220 is coupled.

It will be appreciated that the holes 230 in the upper surface 226 and the lower surface 228 are spaced uniformly. For example, the holes can have substantially uniform spacing along the upper surface 226 and along the bottom surface 228, though in some embodiments, spacing along one or more of the upper surface 226 and the lower surface 228 can vary such that the holes 230 of a single segment 210 are spaced closer than adjacent holes 230 of an adjacent segment. The spacing of the holes 230, in some embodiments, can mimic the spacing of the lateral mass to which the plate 220 is coupled. In some embodiments, hole patterns or the distance between a first hole and a second hole in a set can be approximately 9.5 millimeters, a distance that approximates a length of a lateral mass. One skilled in the art will recognize that this distance can vary based on the type of bone plate used or based on other dimensions of the bone plate. The bone plate 220 can have a width of approximately 5.2 millimeters or 6.7 millimeters, though in some embodiments the width of the bone plate can range from approximately 4 millimeters to approximately 7 millimeters, from approximately 4.5 millimeters to approximately 5.5 millimeters, or have a width of approximately 5 millimeters. A length of the bone plate 220 can vary based on the number of segments 210 included in the bone plate 220 and/or, in some embodiments, a number of bodies to which the bone plate 220 is to be attached.

Figure 11:
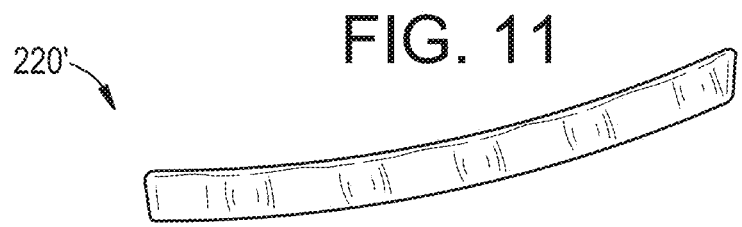
FIG. 11 is a perspective side view of one embodiment of a curved bone plate.

FIG. 11 illustrates an alternate embodiment of the bone plate 220'. For example, in some embodiments, the bone plate 220' can include one or more curved surfaces to allow the bone plate 220' to align with a lateral mass or another location of to which it is fixed. In some embodiments, the bone plate 220' can have a radius of curvature that matches a curve of the spine, e.g., cervical lordosis, to align the plate with the lateral masses. It will be appreciated that the radius of curvature can range from, for example, about 100 to about 130 millimeters.

Figure 12:
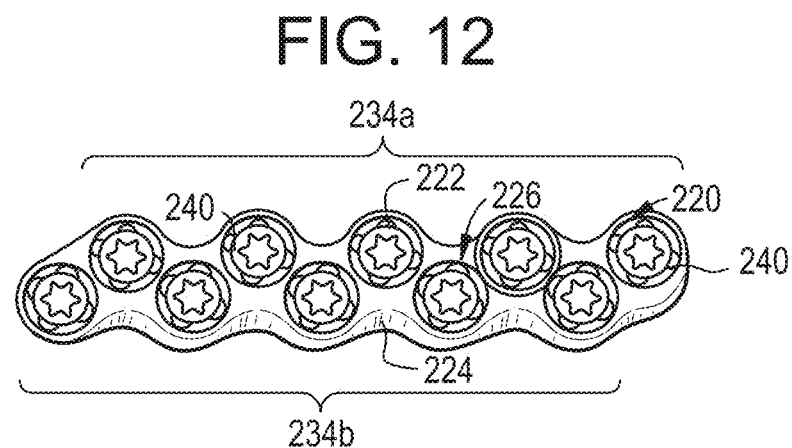
FIG. 12 is a perspective top view of one embodiment of a plating system that includes a bone plate having attachment members disposed therein.
Figure 13:
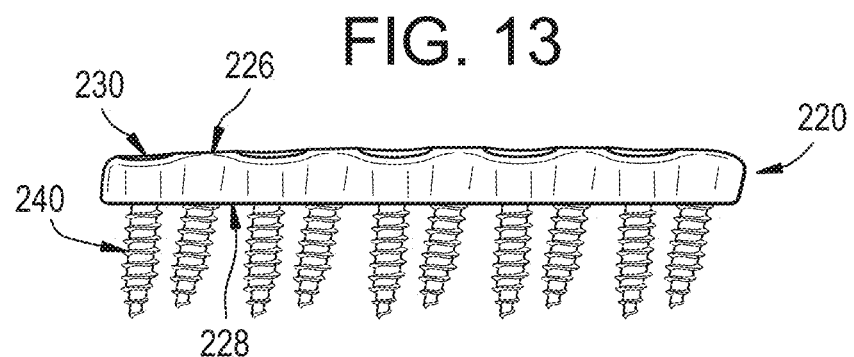
FIG. 13 is a perspective side view of the plating system of FIG. 12.

FIGS. 12 and 13 illustrate the bone plate 220 having the attachment members 240 disposed therein. For example, a hole axis of the first set 234a can be angled approximately 10 degrees cranially in the sagittal plane and laterally in the transverse plane, while a hole axis of the second set 234b can be angled approximately 10 degrees cranially in the sagittal plane. The bone plate 220 can be a medialized lateral mass plate that can be used in less invasive approaches and fixation to the spine. The bone plate 220 can be placed such that the first set 234a faces medially and the second set 234b faces laterally to account for the curvature of the space and to position the attachment members for coupling to boney structures.

The attachment members 240 are disposed within the holes 230 of the bone plate 220. As shown, every hole 230 of the bone plate 220 can include an attachment member 240 therein for multipoint fixation of the bone plate 220 having two holes per segment, though, in some embodiments, the bone plate 220 can include three or more holes 230 per segment. Further, in some embodiments, one or more holes 230 of certain segments of the bone plate 220 can be free from having any attachment members 240 disposed therein without impairing securement of the bone plate 220 to the underlying structure. The holes 230 of the bone plate 220 are configured to receive bilaterally angled attachment members 240 having an up/out trajectory, as mentioned above, that can increase securement of the bone plate 220 to underlying structures, thereby allowing the bone plate to have greater resistance to pull-out. The attachment members 240 in each set 234a, 234b are different as the holes 230 are angled to receive appropriately shaped attachment members 240. The attachment members 240 received therein are self-drilling screws, as discussed in detail above, though it will be appreciated that any of the above-described variations of attachment members can be used with this embodiment.

Figure 14:
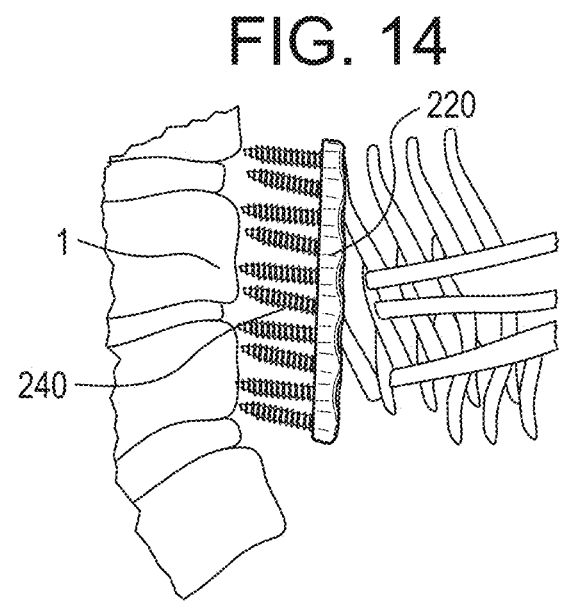
FIG. 14 is a perspective view of an exemplary embodiment of the plating system of FIG. 12 disposed in a patient.

Implantation of the bone plate 220 and the attachment members 240 in bone 1 is shown in detail in FIG. 14.

It will be appreciated that the bone plates generally disclosed herein can be formed in a variety of ways. In some embodiments, one or more portions of the bone plates can be machined, three-dimensionally printed, welded, and so forth. In some embodiments, one or more portions of the bone plate can be chemically etched, which can allow for manufacturing more complex geometries of the bone plates, while avoiding the complexities associated with machining the bone plate.

Figure 15:
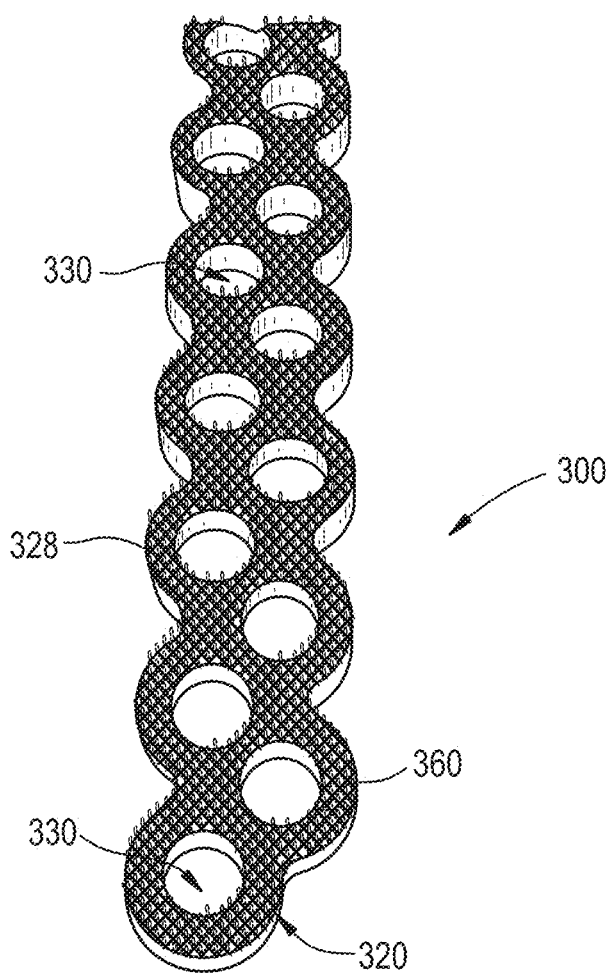
FIG. 15 is a perspective top view of another embodiment of a bone plate having a mesh construct thereon.
Figure 16:
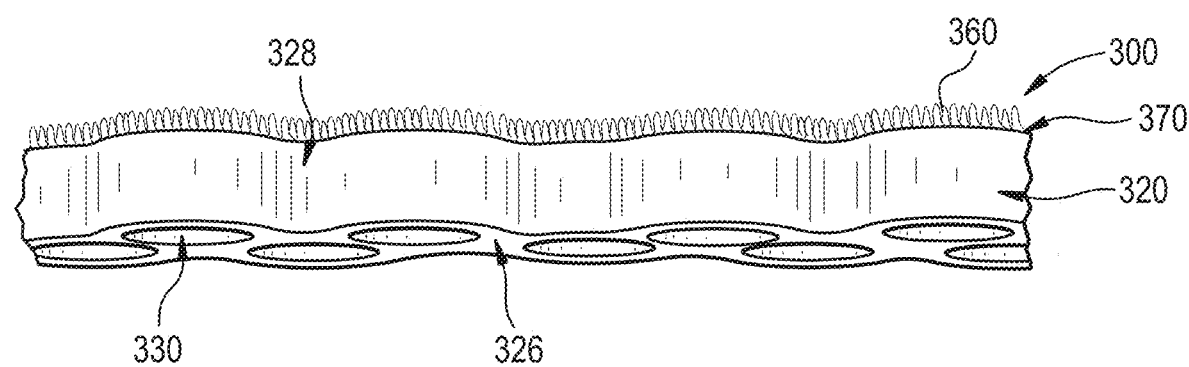
FIG. 16 is a perspective side view of the bone plate of FIG. 15.

FIGS. 15-17 illustrate an exemplary embodiment of a bone plating system 300 that includes a bone plate 320 having a mesh material 360 thereon. As shown in FIG. 16, the mesh material 360 can form a lower portion or base 370 of the bone plate 320. The mesh material 360 can be positioned around one or more holes 330 of the bone plate 320 to provide added thickness throughout the bone plate. In some embodiments, the mesh material 360 can extend from a bone-contacting surface 328 of the bone plate 320 to increase a thickness of the bone plate, as shown, though, in some embodiments, the mesh material 360 can extend from an opposing surface 326 of the bone plate. In other embodiments, the bone plate 320 can be made entirely from the mesh material 360.

Figure 17A:
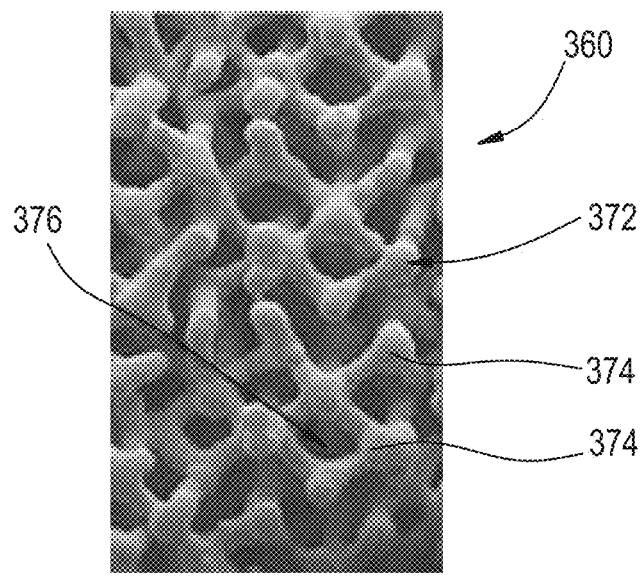
FIG. 17A is a magnified detailed view of the mesh construct of the bone plate of FIG. 15.
Figure 17B:
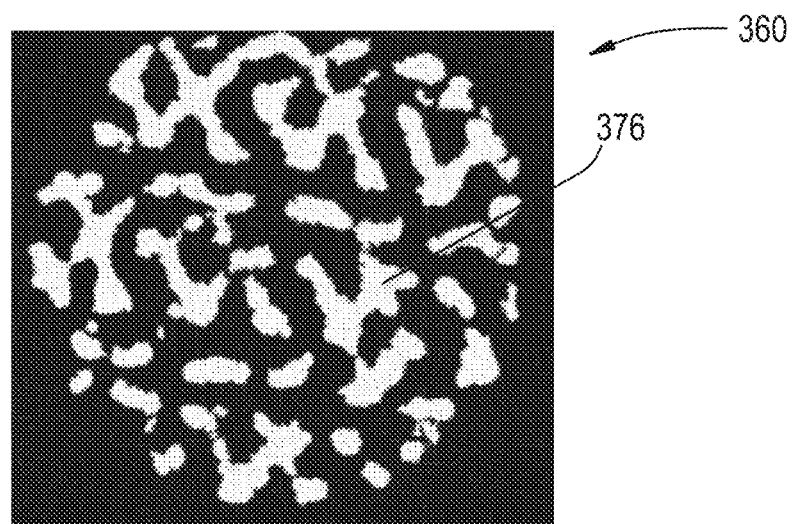
FIG. 17B is a schematic detailed view of the mesh construct of FIG. 17A.

FIGS. 17A and 17B illustrate the mesh material 360 of the lower portion 370 in greater detail. The mesh material 360 can be a porous structure 372 made from titanium, titanium alloy, magnesium, hydroxyapatite, and/or another material by additive manufacturing, e.g., 3D printing. As shown, the porous structure 372 of the lower portion 370 can have a rhombal geometry. For example, the porous structure 372 can be made up of titanium struts 374 that form interconnected rhombal windows 376 therebetween. The rhombal windows 376 can allow for bone in growth through the lower portion 370 to aid in fixation of the bone plate 320. The struts 374 can form a system of interconnected channels, as shown in FIG. 17B, that allow materials to pass therethrough. An amount of materials passing through the bone plate 320 can vary based on a thickness of the bone plate. A thickness of the bone plate that is chemically etched can be narrower than one that is machined. Chemical etching can be used to create a rough surface that can prevent slippage of the bone plate 320 along a surface of the bone and/or allow for bony on-growth and in-growth on the bone plate 320 of various thickness, e.g., about 2.5 millimeters thick. In some embodiments, the rough surface created by chemical etching can range from about 0.1 millimeters to about 0.5 millimeters.

As discussed above, the plating system and the bone plates disclosed herein present a lower profile, less invasive form of lateral mass fixation and longitudinal stabilization that allows multipoint fixation in a single lateral mass. In some embodiments, the bone plate can be used in combination with other devices and/or structures in surgeries that further stabilize portions of the spine. For example, the bone plate 320 can be attached to posterior cervical plates to stabilize and immobilize the plates relative to one another.

Figure 18:
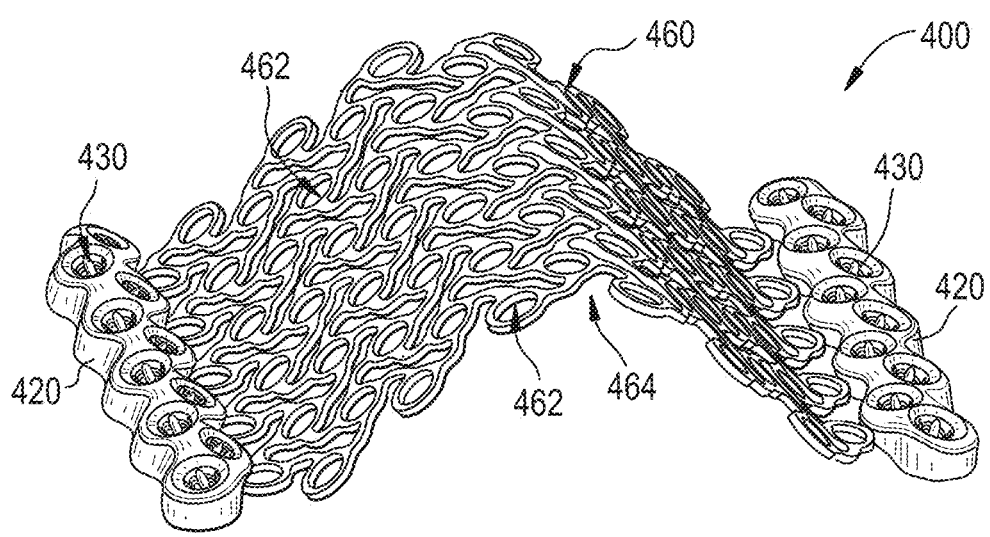
FIG. 18 is a perspective view of one embodiment of a plating system having two bone plates and a mesh construct extending therebetween.

FIG. 18 illustrates another exemplary embodiment of a plating system 400 that includes bone plates 420 and a mesh construct 460. The bone plate 420 can include a mesh construct 460 coupled thereto for cushioning and/or protecting lateral mass structures. The mesh construct 460 can cover the spinal cord following procedures that present a risk to the patient by exposing the spinal cord. For example, the mesh construct 460 can arch over the spinal cord after a laminectomy, which involves removal of the lamina and spinous processes in order to expose the dura covering the spinal cord, leaving the spinal cord exposed.

As shown, the mesh construct 460 can extend between two bone plates 420. The mesh construct 460 can include a pattern having one or more openings 462 extending along a length thereof. The pattern can repeat along an entire surface of the mesh construct 460, as shown, or the pattern can vary along a length of the mesh construct 460. In some embodiments, the openings 462 can be sized to receive an attachment member or another element therethrough for further securing the mesh construct 460 to the posterior cervical spine or other bodies, as described further below.

In use, the bone plates 420 can be secured on opposite sides of the removed lamina, with the mesh construct 460 extending therebetween. The mesh construct 460 can serve as a tissue reattachment point for suturing tissue to the midline to improve recovery time and promote better healing. One or more of the bone plate 420 and/or the mesh construct 460 can be integrally formed or otherwise joined to one another by gluing, welding, clipping, or another means of securement known to one in the art. The mesh construct 460 and/or the bone plate 420 can be manufactured using any of a variety of techniques, including, for example, three-dimensional printing or welding.

In some embodiments, the plating system can include a coating thereon for preventing adhesions. The coating can be applied to a tissue-engaging surface 464 of the bone plate 420 or the mesh construct 460 to minimize tissue attachment to the plating system 400. In some embodiments, for example, the coating can be made from a porous polyethylene material, e.g., SynPor, which is a synthetic, non-resorbable, porous implant material that is made of ultra-high molecular weight polyethylene, featuring a network of open and interconnecting pores. Coatings having such properties can prevent adhesion to the bone plates 420 and the mesh construct 460 can allow the plating system 400 to minimize damage to surrounding tissues when inserted into the patient.

Figure 19:
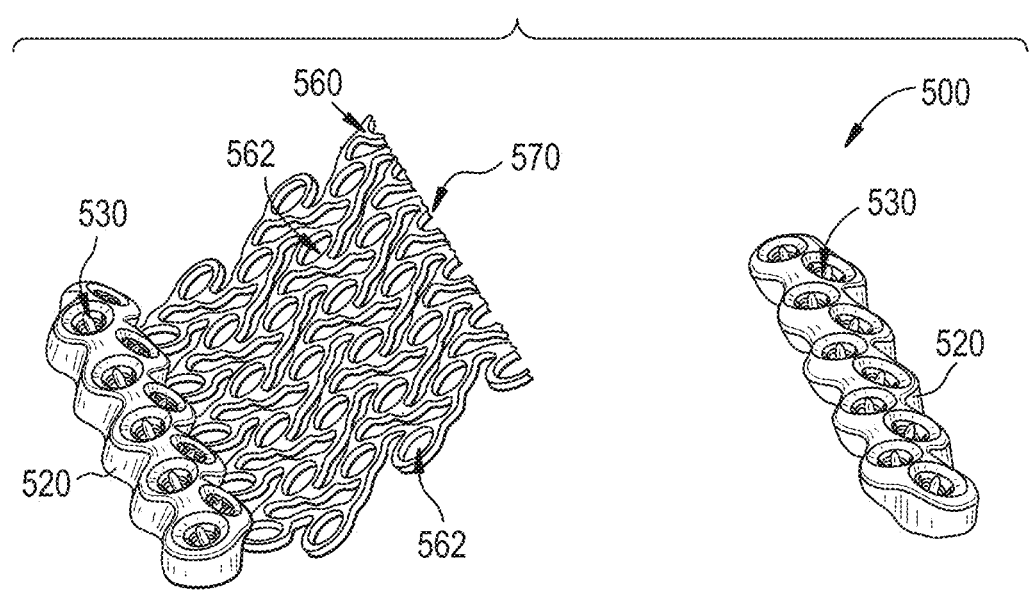
FIG. 19 is a perspective view of one embodiment of a plating system having two bone plates and a mesh constructing extending from one of the bone plates.

FIG. 19 illustrates an alternate embodiment of a bone plating system 500 that includes bone plates 520 and a mesh construct 560. As shown, the mesh construct 560 can be largely the same as that of FIG. 18, except the mesh construct 560 can be coupled to a single bone plate 520 and include a free end 570 that is uncoupled to other structures. This plating system 500 can have a lower profile than the plating system 400 of FIG. 18, and can be used, for example, in a laminoplasty, where a lamina is cut and repositioned to enlarge the spinal canal, which eases pressure on the spinal cord and preserves the posterior arch. In use, one of the bone plates 520 can be fixed to the spine where the lamina was retained and the mesh construct can extend therefrom and bridge between the cut lamina ends. The free end 570 of the mesh construct 560 can be secured to the posterior arch or another body surface by inserting one or more attachment members through the openings of the mesh construct. In some embodiments, one or more openings 562 formed in the mesh construct 560, e.g., the openings near the free end, can include locking threads (not shown) for receiving the attachment members therein. The mesh construct 560 can receive lag screws therein for securing the mesh construct 560, though, in some embodiments, due to risk of back-out, locking screws can be used to secure the mesh construct 560 at the surgical site.

Figure 20:
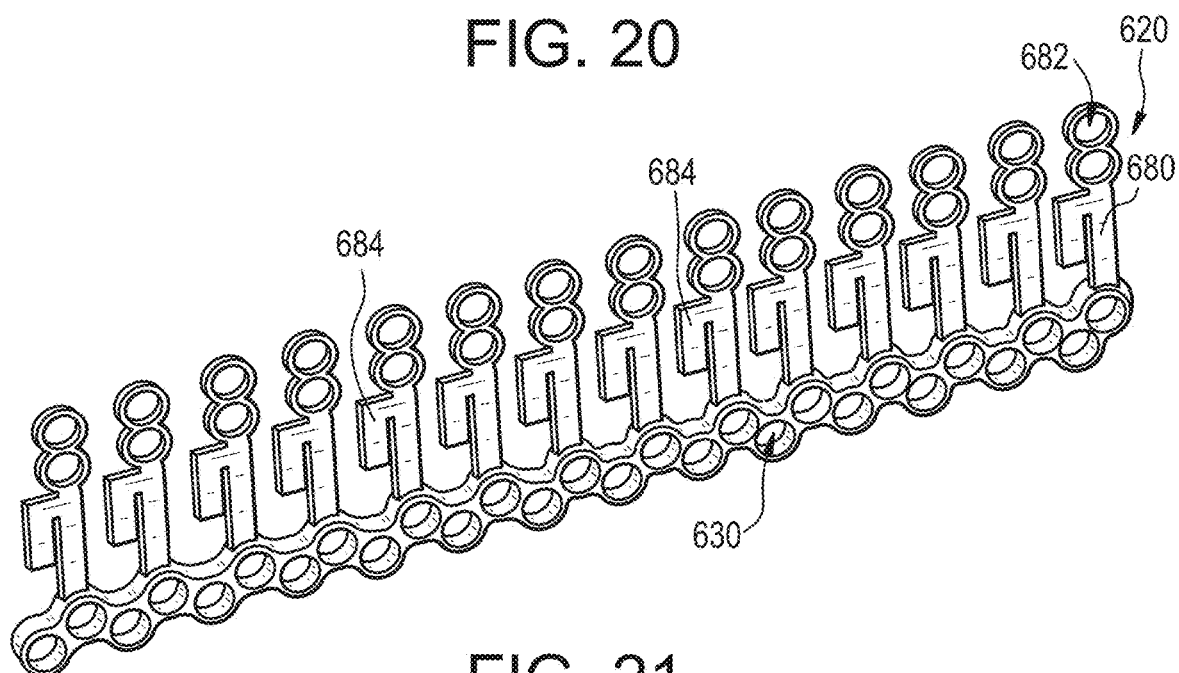
FIG. 20 is a perspective view of one embodiment of a bone plate having tabs extending therefrom.
Figure 21:
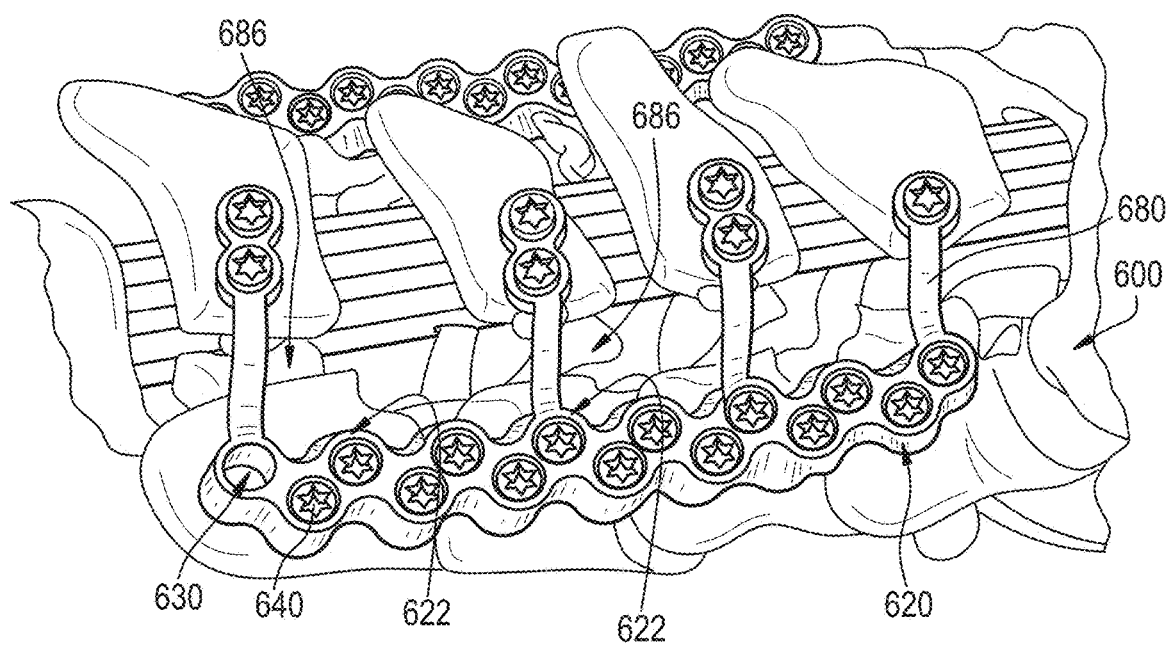
FIG. 21 is a perspective view of the bone plate of FIG. 20 coupled to bony structures of a patient.

FIGS. 20 and 21 illustrate an alternate embodiment of a bone plate 620 that can be used as part of a bone plating system 600 in surgical procedures, e.g., laminoplasty. The bone plate 620 can include one or more tabs 680 protruding from one of the surfaces of the bone plate 620 for bridging between cut lamina ends. The tabs 680 can protrude medially from the bone plate 620, as shown in FIG. 21, and bend up in the posterior direction to form the bridge between the vertebral bodies and cut lamina ends. The tabs 680 can protrude from each node 622 of the bone plate 620, though, in some embodiments, the tabs 680 can protrude from every other node or from various nodes, as shown in FIG. 21. The tabs 680 can be integrated into the bone plate 620 such that the tabs 680 are integral with the bone plate 620, though, in some embodiments, the tabs 680 can alternatively attach and detach from nodes 622 when being coupled to the bone plate 620.

The tabs 680 can include one or more openings 682 formed therein for securing the tabs 680 to a cut lamina end or a neighboring body. As shown, the openings 682 can be positioned on a distal end of the tab 680 opposite of the end coupled to the bone plate 620. The openings 682 can be positioned to allow the multipoint fixation within the cut lamina ends. In some embodiments, the openings 682 can be aligned along a longitudinal axis of the tab 680 such that the openings 682 are positioned in the same plane as the tab 680. As shown, the openings 682 can be sized to receive attachment members therein to secure the tabs 680 to the cut lamina ends.

In some embodiments, the tabs 680 can have one or more wings 684 extending therefrom. The wings 684 can be bent in various directions to support the structures to which the tabs 680 are coupled. For example, in some embodiments, the wings 684 can be bent up under the cut lamina ends to support the lamina ends during the surgical procedure, e.g., during screw insertion. By supporting the lamina ends, the force of the screw insertion is prevented from pushing the posterior arch down onto the cord, thereby preventing damage to the spinal cord or its surrounding tissues. In some embodiments, bone graft can be packed in the spaces 686 between the laminae to bridge between adjacent vertebral levels.

Stabilization of the laminae in a desired position after laminotomy, e.g., laminoplasty, and/or laminectomy, is important to preserve the posterior arch and prevent damage to the spinal cord. For example, portions of the laminae can be cut and secured by the plating systems 200, 300, 400, 500, 600 described herein to relieve pressure on the spinal cord and/or treat conditions, such as cervical stenosis. Due to their frequent implantation in proximity to the spinal cord and being subjected to heavy loads, it is important that bone plates that are secured to the neighboring lateral masses and the laminae are firmly held in place and that the attachment members used to secure the bone plates do not come loose. Use of the tabs 680 and wings 684 to bridge cut portions of the laminae can minimize these risks.

The bone plate plating systems discussed above can include additional locking features that help secure bone plates in place. The locking features can increase stability of the bone plating systems at the implantation site, thereby preventing unintentional back-out and slippage of the bone plates. For example, the locking features can include conical locking threads that prevent slippage and decoupling. In some embodiments, the attachment members can be fixed in an angled trajectory to promote fixation. In some embodiments, multiple attachment members can be used to fix the bone plate, and the attachment members can be placed in divergent and/or convergent positions relative to one another to provide enhanced fixation and higher pull-out resistance. It will be appreciated that the locking features can be used alone or in combination with any features discussed above, e.g., attachment members 140, 240, tabs 680, and so forth.

Figure 22:
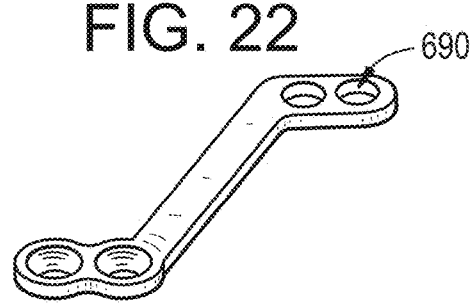
FIG. 22 is a schematic perspective view of one embodiment of additional locking features of a bone plate.
Figure 23A:
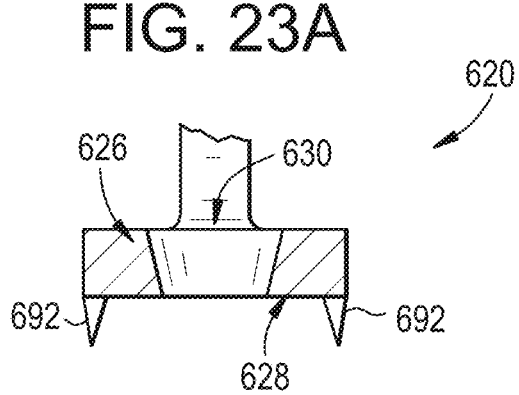
FIG. 23A is schematic side view of another embodiment of additional locking features of a bone plate.
Figure 23B:
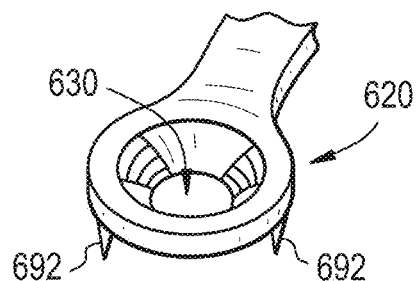
FIG. 23B is schematic perspective view of the additional locking features of the bone plate of FIG. 23A.
Figure 24:
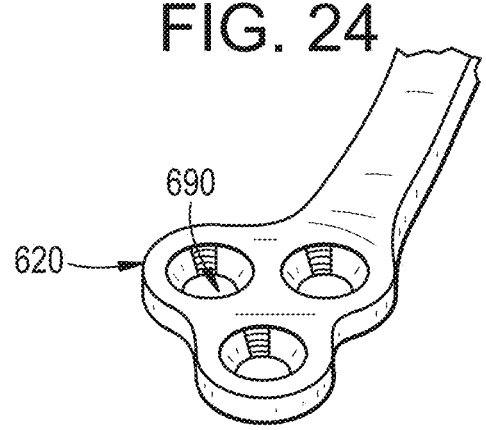
FIG. 24 is a schematic perspective view of another embodiment of a bone plate having additional locking features.

FIGS. 22-24 illustrate exemplary embodiments of these locking features. For example, in some embodiments, the bone plate can include locking compression plate (LCP) holes 690 therein for added fixation. As shown, the LCP holes 690 can be positioned on an opposite side of a bone plate and/or tab to ensure an entire length of the bone plate and/or tab is secured. The LCP holes can function as auxiliary holes that minimize damage to underlying structures while ensuring an entire length of the bone plate and/or tab is sufficiently secured such that outside forces do not loosen the plate from the structures, causing unwanted damage.

FIGS. 23A and 23B illustrate an alternate embodiment of the locking features. The locking features can include one or more spikes 692 protruding from a bottom surface 628 thereof. The spikes can implant into the lateral mass to prevent rotation, and promote fixation, of the bone plate 620 with respect to the lateral mass. As shown, the bone plate 620 can include two spikes 692 positioned on opposite sides of the bone plate 620 along a circumference of the hole 630, though, it will be appreciated that, in some embodiments, a single spike 692 or three or more spikes 692 can be used to secure the bone plate. In some embodiments, the multiple holes can each have one or more spikes 692 protruding therefrom for fixation on the lateral mass.

FIG. 24 illustrates an alternate embodiment of the locking features that have multiple openings 690 thereon for multi-point fixation. As shown, a portion of the bone plate 620 can include three openings 690 to promote increase fixation. The openings 690 can be placed in a triangular orientation with respect to one another to provide for more points of fixation between the bone plate 630 and the boney structures in a limited space. It will be appreciated that, in some embodiments, bone plates having four or more openings can be used. The openings 690 can be positioned at various angles with respect to one another. As discussed above with respect to the tabs 680, the openings 690 can be aligned with a longitudinal axis of the bone plate 620, though, in some embodiments, the openings 690 can be angled with respect to one another. The relative angle between the openings 690 can range from about 0 degrees to about 90 degrees, or from about 30 degrees to about 60 degrees. It will be appreciated that the angle of the bone plate can depend on whether the plate is being fixed to the lateral mass or the laminae. In some embodiments, the locking features can include fixation points for bone graft material to promote bone ingrowth.

FIGS. 25-28 illustrate exemplary embodiments of procedures that implement the above-described systems and/or devices. Except as indicated below and will be readily appreciated by one having ordinary skill in the art, the steps of the described methods and the devices used in the minimally-invasive surgery techniques discussed below can be performed in various sequences, with one or more steps can be omitted or added. Further, it will be appreciated that any of the above-described bone plating systems and/or bone plates can be used with the techniques discussed below. A detailed description of every sequence of steps, and every system and/or device used, is omitted here for the sake of brevity. It will be appreciated that one or more of the methods disclosed herein can be performed simultaneously with the other methods.

Figure 25:
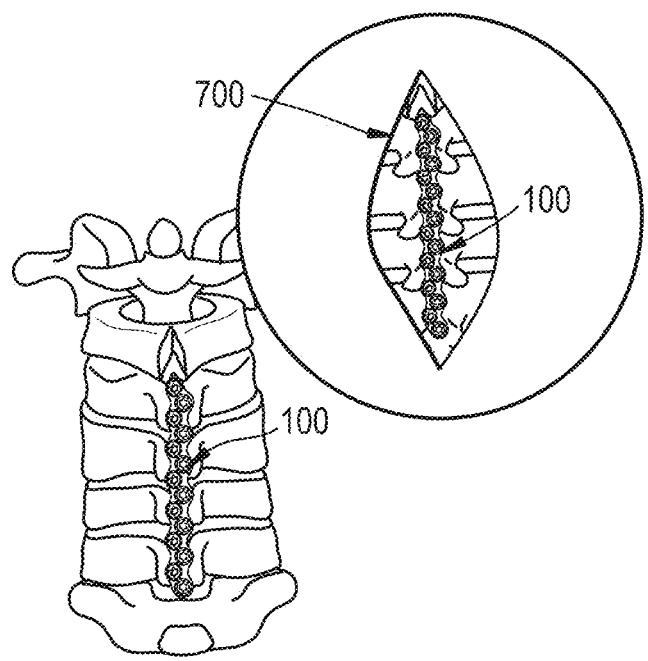
FIG. 25 is a perspective top view of one embodiment of a bone plate coupled to a spinous process of a patient.

FIG. 25 illustrates an exemplary embodiment of a minimally-invasive surgery technique in which one of the above-mentioned bone plating systems 100 is coupled to the spinous process. As shown, an incision 700 can be made along a midline of the spine to expose the spinous process in the surgical site to couple the bone plating system thereto. Making a midline incision 700 minimizes invasiveness of the procedure by substantially avoiding dissection to the lateral aspect of the lateral mass, which requires an incision that is approximately 38 millimeters in width, as well as minimizes retraction and muscle stripping that can occur in alternate procedures. Once the spinous process is exposed, the spinous process, as well as the neighboring tissue, can be shaved and/or cut down to a flat plane. In some embodiments, a rib cutter (not shown) can used to shave the spinous process to a single plane that can support the plating system. After the surgical site is sufficiently prepared, one or more of the above-described bone plating systems 100 can be positioned along the spinous process and secured thereto using one or more of the above-described attachment members.

A width of the incision 700 down the midline to the upper spinous process can vary based on anatomy of the patient, pathology, and/or the preference of the surgeon. For example, a width of the incision 700 down the midline to the upper spinous process can range from approximately 10 millimeters to 30 millimeters or range from approximately 15 millimeters to 25 millimeters. In some embodiments, the width of the incision 700 can range from approximately 6 millimeters to approximately 12 millimeters, range from approximately 7 millimeters to approximately 10 millimeters, or have a value of approximately 8 millimeters. In some embodiments, the width of the incision 700 can be substantially the same as a width of the spinous process, e.g., approximately 8 millimeters in adults and smaller in children. For example, a ratio of the incision width to the spinous process width can be approximately 1:1, approximately 1:1.25, approximately 1:1.5, approximately 1:1.75, approximately 1:2.0, and so forth. In some embodiments, a width of the incision 700 can be based on a width of the bone plate. For example, a ratio of the incision width to the bone plate width can be approximately 1:1, approximately 1:0.75, approximately 1:0.5, and so forth. It will be appreciated that in some embodiments, a ratio of the incision width to the bone plate width can be approximately 1:1.25, approximately 1:1.5, approximately 1:1.75, approximately 1:2.0, and so forth.

The attachment members can be driven into the bone plate 120 using a straight-in trajectory due to an abundance of bone in the spinous process which would prevent unintentional back-out of the attachment members, though, in some embodiments, bilaterally angled attachment members can be used.

Figure 26:
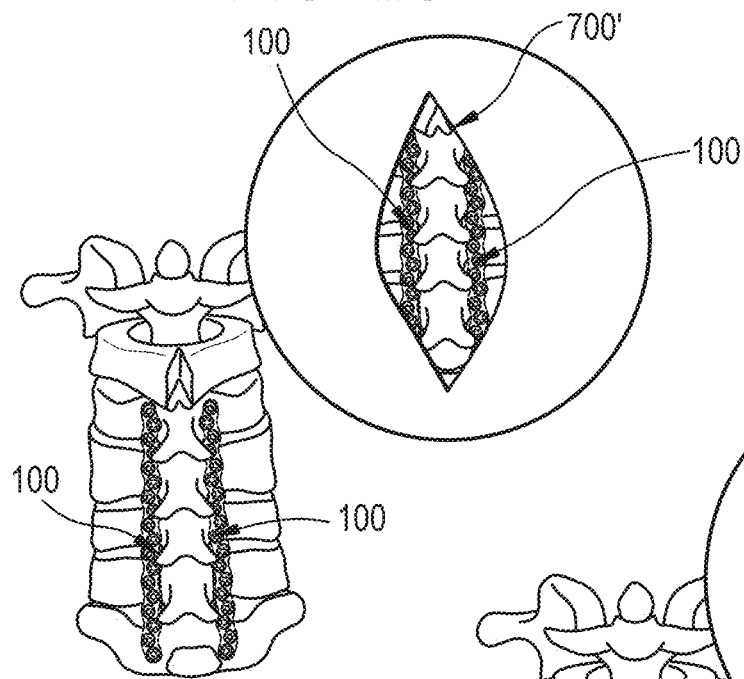
FIG. 26 is a perspective top view of one embodiment of two bone plates coupled to laminae of a patient.

FIG. 26 illustrates an alternate embodiment of a minimally-invasive surgery technique in which one of the above-mentioned plating systems 100 is coupled to one or more laminae. As shown, an incision 700' is made along the midline to expose one or more of the laminae and tissue is retracted from the medial to lateral mass on both side of the spinal cord. Although the upper lamina is shown, in some embodiments, the incision 700' can be performed to expose various portions of the laminae, e.g., the lower lamina. After the surgical site is sufficiently prepped, one or more of the above-described bone plating systems can be positioned along the upper lamina and secured thereto using one or more of the above-described attachment members. As shown, the bone plates 120 of the bone plating system 100 can be placed on bilateral sides of the spinal cord, though, in some embodiments, a single bone plate can be inserted.

A width of the incision 700' down the midline to the upper lamina can vary based on anatomy of the patient, pathology, and/or the preference of the surgeon. For example, a width of the incision 700' down the midline to the upper lamina can range from approximately 10 millimeters to 30 millimeters or range from approximately 15 millimeters to 25 millimeters. In some embodiments, the width of the incision 700' can range from approximately 16 millimeters to approximately 22 millimeters, range from approximately 17 millimeters to approximately 20 millimeters, or have a value of approximately 18 millimeters. In some embodiments, the width of the incision 700' can be a function of the lamina width. For example, a ratio of the incision width to the lamina width can be approximately 1:1, approximately 1:1.25, approximately 1:1.5, approximately 1:1.75, approximately 1:2.0, and so forth. In some embodiments, a width of the incision 700' can be based on a width of the bone plate. For example, a ratio of the incision width to the bone plate width can be approximately 1:1, approximately 1:0.75, approximately 1:0.5, and so forth.

Figure 27:
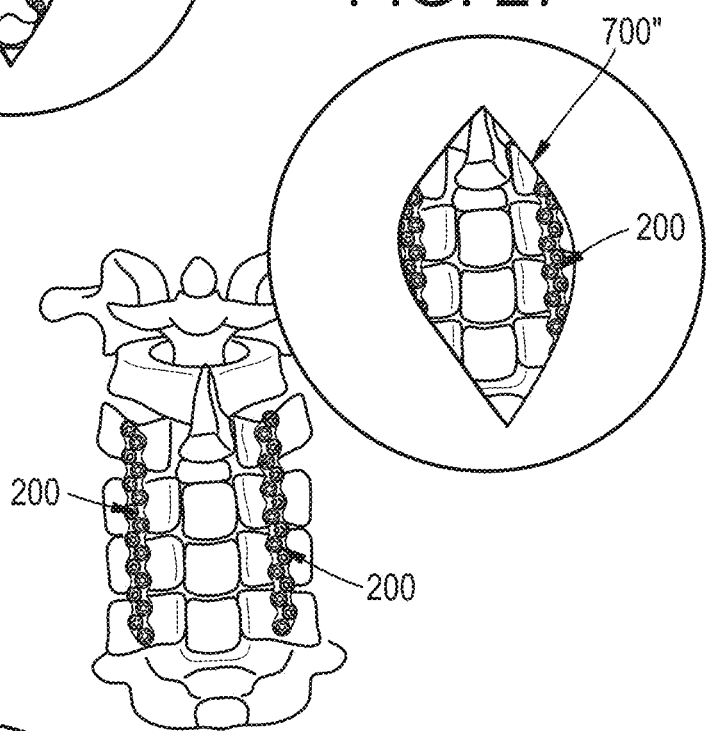
FIG. 27 is a perspective top view of one embodiment of two bone plates coupled to lateral masses of a patient.

FIG. 27 illustrates an alternate embodiment of a minimally-invasive surgery technique in which one of the above-mentioned bone plating systems is used in a procedure to decompress the spinal cord, e.g., a laminectomy. As shown, an incision 700" is made along the midline to expose one or more of the lamina and tissue is retracted from the medial to lateral mass on both sides of the spinal cord. After the surgical site is sufficiently prepared, one or more bone plating systems 200, such as the systems shown in FIGS. 10A-13, can be placed to hug the medial-most aspects of the lateral mass and secured thereto using one or more of the above-described attachment members. As shown, the bone plating system 200 can be placed on bilateral sides of the spinal cord, though, in some embodiments, a single bone plate can be inserted. It will be appreciated that while FIGS. 10A-13 are being discussed as examples with regard to this embodiment, one or more of the above-described bone plating systems 100, 300, 400, 500, 600 can be used in lieu of, or in addition to, the instantly disclosed bone plating system.

A width of the incision 700" down the midline to the upper lamina can vary based on anatomy of the patient, pathology, and/or the preference of the surgeon. For example, a width of the incision 700" down the midline to the upper lamina can range from approximately 10 millimeters to 30 millimeters or range from approximately 15 millimeters to 25 millimeters. In some embodiments, the width of the incision 700" can range from approximately 26 millimeters to approximately 32 millimeters, range from approximately 27 millimeters to approximately 30 millimeters, or have a value of approximately 28 millimeters. In some embodiments, the width of the incision 700" can be a function of the lateral mass. For example, a ratio of the incision width to the lateral mass can be approximately 1:1, approximately 1:1.25, approximately 1:1.5, approximately 1:1.75, approximately 1:2.0, and so forth. In some embodiments, a width of the incision 700" can be based on a width of the bone plate 220. For example, a ratio of the incision width to the bone plate width can be approximately 1:1, approximately 1:0.75, approximately 1:0.5, and so forth. It will be appreciated that the instantly disclosed incision 700" is smaller than traditional incisions to perform the procedure, and results in approximately half the exposure of the lateral mass than standard procedures.

The attachment members 240 can be driven into the bone plate 220 as discussed above with respect to FIGS. 12 and 13. For example, the hole axis $H_A$ of a medial set of holes (e.g., see first set 234a of holes 230 in FIG. 10A) can be angled approximately 10 degrees cranially in the sagittal plane and approximately 10 degrees laterally in the transverse plane, while the hole axis $H_B$ of the lateral set of holes (e.g., see second set 234b of holes 230 in FIG. 10A) is angled approximately 10 degrees cranially in the sagittal plane. The trajectory of the variable angle attachment members 240 disposed in the holes 230 allow the plate to be closer to the midline to minimize lateral exposure and retraction of the tissue at the surgical site.

Figure 28:
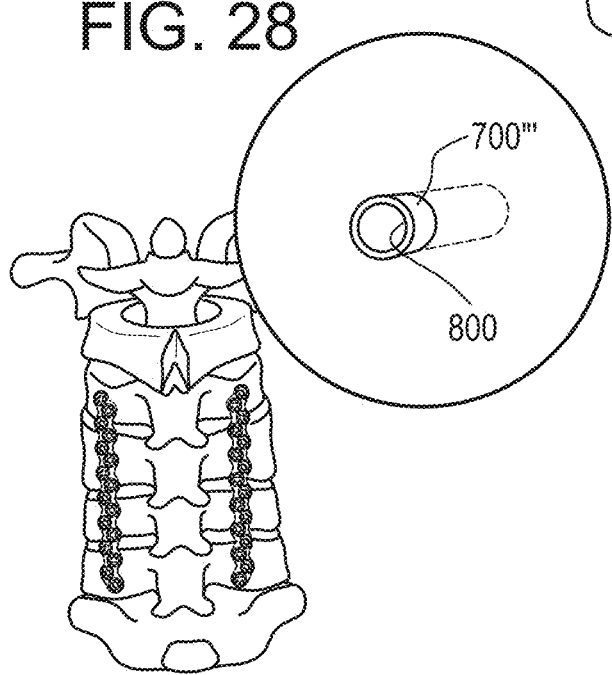
FIG. 28 is a perspective top view of one embodiment of two bone plates coupled to lateral masses of a patient via an access tube inserted percutaneously into a patient.

FIG. 28 illustrates an embodiment of a minimally-invasive surgery technique in which one of the above-mentioned plating systems is introduced through a single incision and access port or tube. As shown, the incision 700''' can be made to designate a target surgical site and an access tube 800 can be inserted percutaneously therethrough. In some embodiments, there is dilation over a navigated probe to prepare the surgical site for the access tube 800 being inserted therein. Sequential dilation up to the preferred size access tube is then performed. The access tube is then introduced over the associated dilator. In one embodiment, the initial anchoring is in the disc space and concentric sequential dilation device(s) would be used in order to retract tissue concentrically around the initial anchoring point. The dilator can remain within the target surgical site or can be removed, leaving the access tube in place.

It will be appreciated that for the minimally-invasive surgery applications discussed herein, the above-described bone plating systems 100 can be introduced through the incisions and moved relative to the skin surface such that the skin aligns with the systems 100 at a desired location by moving the plate and the skin relative to one another.

Figure 29:
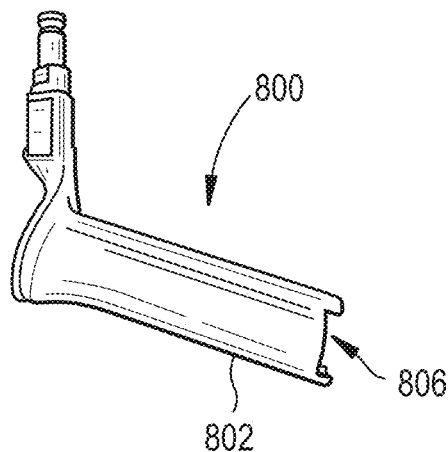
FIG. 29 is a side view of one embodiment of an access tube having a port extending therefrom.
Figure 30:
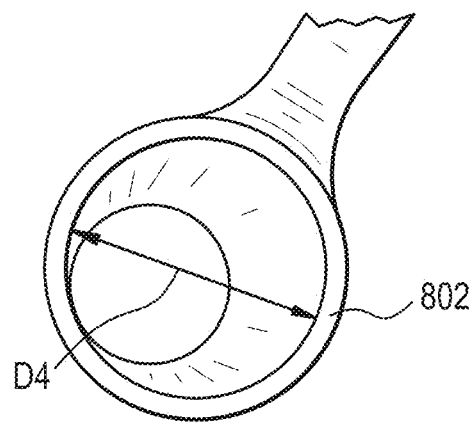
FIG. 30 is a perspective top view of the access tube of FIG. 29.
Figure 31:
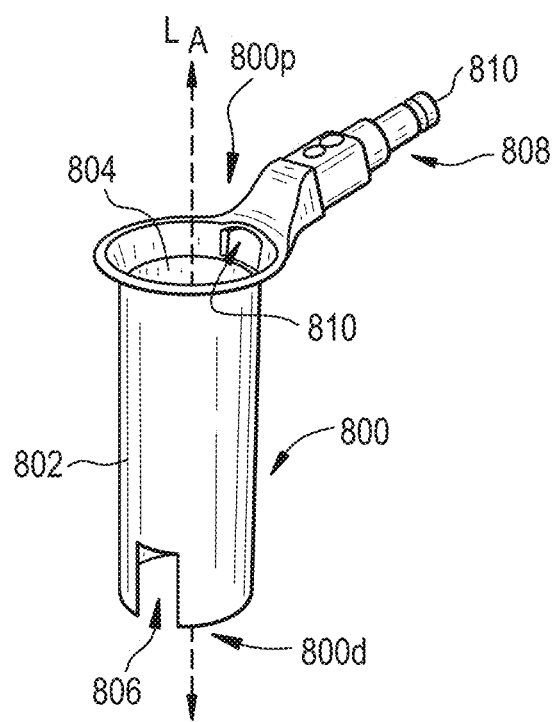
FIG. 31 is a perspective view of the access tube of FIG. 29.

FIGS. 29-31 illustrate an exemplary embodiment of the access tube 800 in greater detail. The access tube 800 can include a body 802 defining a channel 804 having a longitudinal axis $L_A$ extending therein. The access tube 800 can be hollow to allow one or more tools, instruments, and/or objects to pass therethrough. Once implanted in the surgical site, the access tube 800 can receive the bone plate, the attachment members, and so forth for implanting in the surgical site. As shown, the access tube 800 can remain implanted within the patient after the dilators have been removed. For example, the access tube 800 can be implanted at a location along, or in proximity to, the spinal cord to provide an access path to the spine and/or the remainder of the surgical site.

Figure 34:
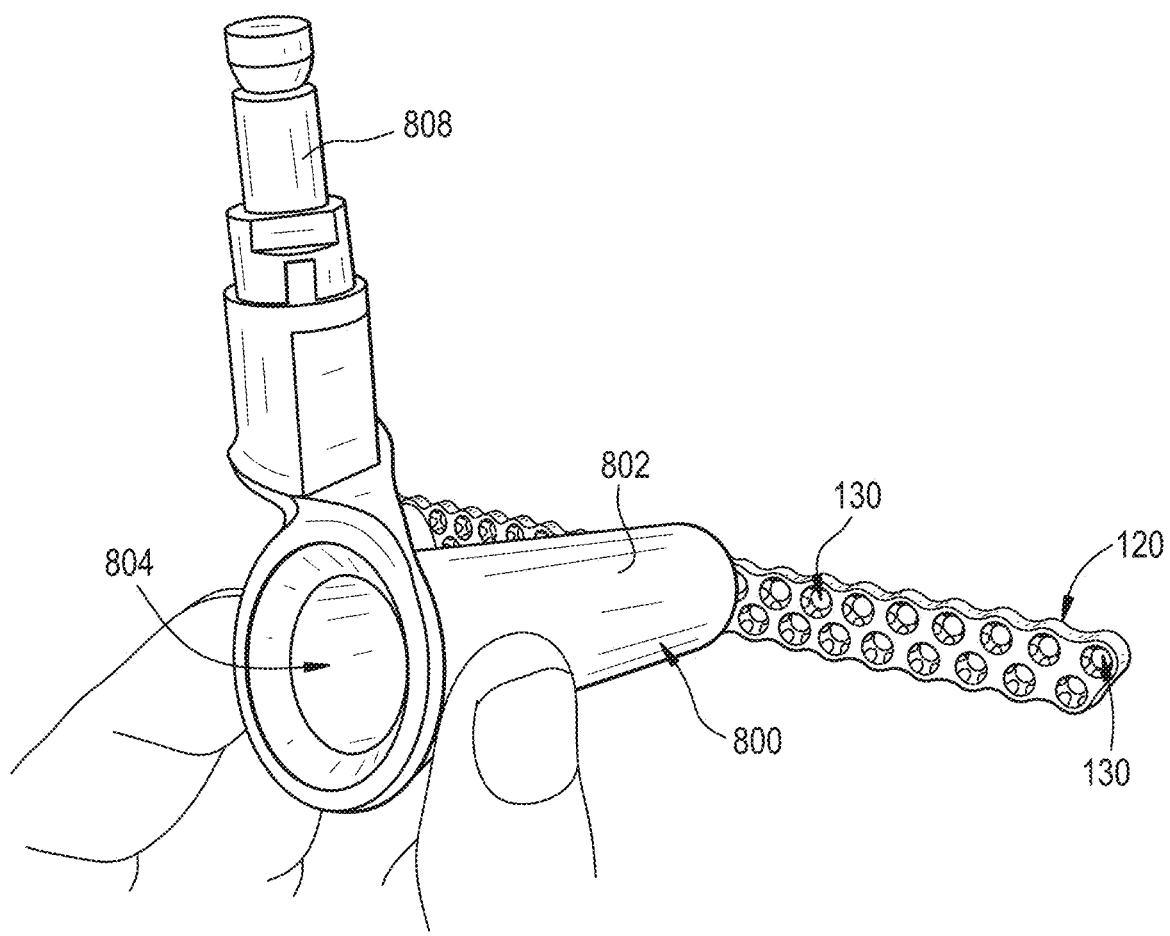
FIG. 34 is a perspective view of the access tube of FIG. 29 disposed with relation to the bone plate of FIG. 2.

The access tube 800 can include a cut-out 806 formed therein. As shown in FIG. 31, the cut-out 806 can be formed at a distal end 800d of the access tube 800 to allow larger objects to pass therethrough. For example, the cut-out 806 can also allow for steering of a bone plate within the access tube 800, as well as for attaching the access tube 800 to the bone plate. For example, in some embodiments, the distal end 800d can be positioned along the bone plate 100 such that the cut-out 806 is positioned along the bone plate. The access tube 800 can be slid along the upper surface 126 of the bone plate 100, as shown in FIG. 34, to abut the holes 130 to allow attachment members 140 to be inserted therein. The cut-out 806 can extend through a portion of the body 802 of the access tube 800, as shown, though, in some embodiments, the cut-out 806 can extend through an entire length of the access tube 800 to allow deformation of the tube. In some embodiments, the access tube 800 can include additional cut-outs to allow greater maneuverability for tools passing therethrough.

In some embodiments, the access tube 800 can include one or more couplers 808 thereon for connecting surgical tools thereto. For example, the coupler 808 can protrude from a proximal end 800p of the access tube 800 for coupling to a surgical instrument and/or tools for performing the procedure. As shown in FIG. 31, the coupler 808 can extend at an oblique angle with respect to the channel 804 of the access tube 800 so as not to obstruct the channel. In some embodiments, the coupler 808 can be sized and shaped such that it is received within a recess of a surgical tool being coupled thereto. The coupler 808 can also include a bore 810 that passes therethrough. The bore 810 can be in communication with the channel 804 such that any tool coupled thereto can access the channel 804 and surgical site.

Figure 32:
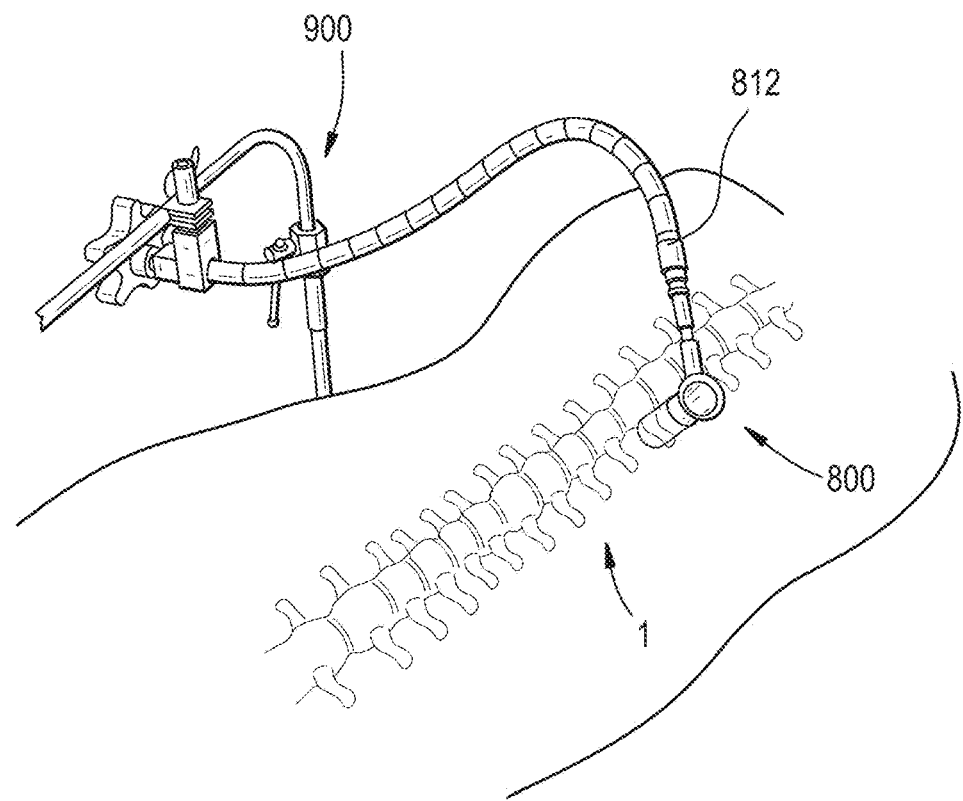
FIG. 32 is a perspective view of the access tube of FIG. 29 inserted into the patient and stabilized using a flex arm.
Figure 33:
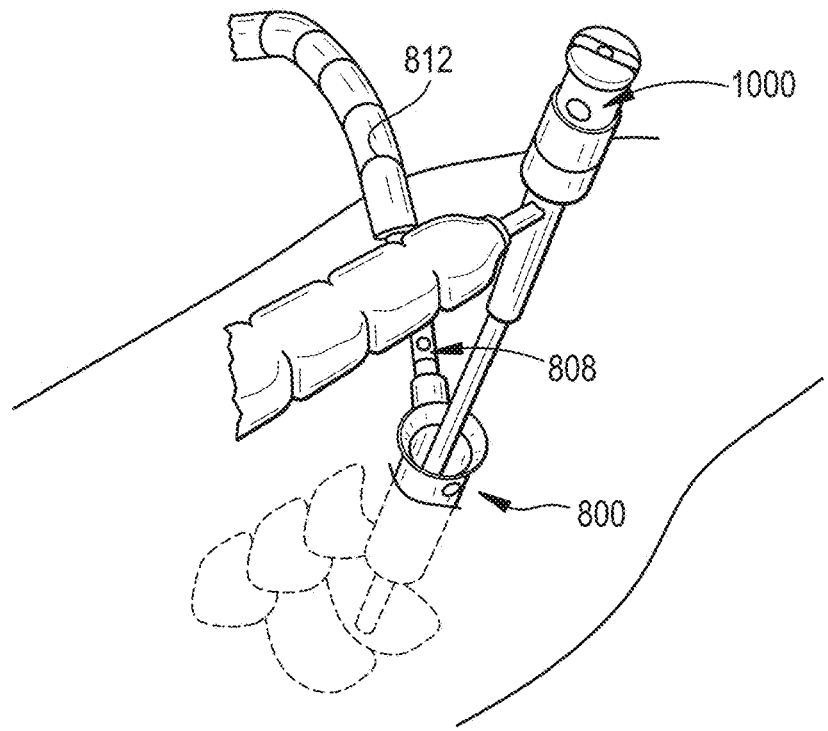
FIG. 33 is a perspective view of the access tube of FIG. 29 receiving a tool therethrough.

FIG. 32 illustrates the access tube 800 implanted within the patient while coupled to a vacuum assembly 900. The access tube 800 can be implanted at a location along, or in proximity to, the spinal cord 1 to provide an access path to the surgical site. For example, the vacuum assembly 900 can be coupled to the tube 800 via the coupler 808 and can extract tissue and other occlusions from the surgical site through the bore 810. The coupler 808 of the access tube 800 can be received in a flex arm 812 of the device, as shown, to couple the access tube 800 thereto. The flex arm 812 can couple to the vacuum assembly 900, as discussed above, to remove tissue and other bodies from the surgical site and hold the access tube 800 in place. In some embodiments, an irrigator, a light source, and so forth can be attached to the coupler 808 in lieu of, or in addition to, the vacuum assembly 900. A tool 1000 can then be inserted through the access tube 800 to perform the procedure, as shown in FIG. 33.

In some embodiments, the access tube 800 can also be used to pass one or more bone plates 100 into the surgical site. It will be appreciated that, in some embodiments, the bone plate 100 can be rotated to orient a longitudinal axis A1 of the bone plate 100 substantially parallel to a longitudinal axis $L_A$ of the tube 800 to pass the bone plate 100 through the length of the tube 800. In some embodiments, a bowie or another cutting instrument (not shown) can be inserted through the access tube 800 either before, during, and/or after passing the bone plate 100 therethrough to dissect tissue from the bone and open a pocket over the bone surface for disposing the bone plate therein.

The access tube 800 can be used to apply a bone plate 120 to each of bilateral sides of the spinal cord. For example, a single incision can be made at a target surgical site, through which both bone plates can be introduced. A second incision can be made, in some embodiments, to facilitate dissection of tissue from the surgical site or insertion of one or more of the bone plate. In some embodiments, the second incision, and the access tube 800 disposed therein, can be made at an opposite end of the target site such that the bone plate 120 is disposed between the two incisions, though the location of the second incision relative to the first incision can vary. Alternatively, the second incision can be made on an opposite side of the midline of the spinal cord to allow for insertion of a second bone plate on an opposite side of the spinal cord. In some embodiments, still further additional incisions having access tubes disposed therein can be utilized if necessary.

Once the bone plate passes through the access tube 800, the bone plate can be rotated to align with the structures at the surgical site, e.g., spinous process, lateral mass, etc. In some embodiments, the width of the incision can be no larger than a diameter of the tube in order to minimize the structural damage to surrounding tissue for minimally-invasive surgery. The diameter of the tube 800 can also be such that the bone plate 120 can pass therethrough. For example, a diameter D4 of the access tube 800 can range from approximately 3 millimeters to approximately 16 millimeters, from approximately 5 millimeters to approximately 15 millimeters, from approximately 8 millimeters to approximately 12 millimeters, or from approximately 9 millimeters to approximately 11 millimeters. In some embodiments, the access tube 800 can be elliptical and/or oval-shaped. In some embodiments a cranial-caudal length of the access tube 800 can be greater than a lateral width of the tube. For example, a ratio of the width of the access tube 800 to a length of the tube can range from approximately 1:1.5 to approximately 1:3, e.g., the access tube 800 having a width of approximately 10 millimeters and a length of approximately 18 millimeters, though these values can vary.

To rotate the bone plate, the cut-out 806 can be positioned in a direction along the structures of the surgical site, e.g., spinous process, lateral mass, etc. As the bone plate passes through the access tube 800, the bone plate can be angled within the access tube such that a distal-most end of the bone plate extends radially beyond the walls of the access tube 800 through the cut-out 806. The bone plate can continue to advance in the direction of the cut-out 806 until a proximal-most end of the bone plate distally exits the access tube 800. The bone plate can then be positioned to align with the structures at the surgical site.

After the bone plate 120 is implanted at the surgical site, the attachment members 140 can then be passed through the access tube 800 to secure the bone plate 120 at the surgical site. As shown in FIG. 34, the channel 804 of the access tube 800 can be positioned over one or more holes 130 of the bone plate 120 to pass the attachment members 140 into the holes. In embodiments in which a second incision is made, the bone plate 120 can be passed through the second access tube subcutaneously to fit into the pocket made by the first access tube, followed by the attachment members 140 being inserted through the first and second access tubes 800 into the holes 130 of the bone plates 120.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The instruments and methods disclosed herein can be used in minimally-invasive surgery and/or open surgery. While the instruments and methods disclosed herein are generally described in the context of spinal surgery on a human patient, it will be appreciated that the methods and instruments disclosed herein can be used in any type of surgery on a human or animal subject, in non-surgical applications, on non-living objects, and so forth.

Although specific embodiments are described above, it should be understood that numerous changes may be made within the spirit and scope of the concepts described. Accordingly, the disclosure is not to be limited by what has been particularly shown and described. All publications and references cited herein are expressly incorporated herein by reference in their entirety.

The invention claimed is:

1. A vertebral plating system, comprising:
a plate having an upper surface, a lower surface, and a plurality of holes that extend from the upper surface to the lower surface, the plate being configured to extend along at least one lateral mass of each of adjacent vertebral levels such that two or more of the plurality of holes define a plurality of fixation points at each lateral mass of the adjacent vertebral levels; and
a plurality of attachment members configured to be inserted through the plurality of holes in the plate and into the lateral masses of each of the vertebral levels to fix the plate to the vertebral levels,
wherein the plurality of holes are arranged in two longitudinal rows such that the holes of a first longitudinal row of holes are offset with respect to a second longitudinal row of holes, with the first longitudinal row having a first central axis and the second longitudinal row having a second central axis,
wherein a central longitudinal axis of the plate passes through at least a portion of each of the plurality of holes,
wherein the upper surface includes one or more spaces formed between a hole from the first longitudinal row of holes and an adjacent hole from the second longitudinal row of holes, the one or more spaces being defined by a portion of the upper surface and lying in a common plane with a plane of the upper surface, the one or more spaces extending between an outermost point of each of the holes across the central longitudinal axis of the plate,
wherein one or more of the holes is threaded such that the threads of at least one of the holes are positioned adjacent to the one or more spaces to increase the strength of the plate, the one or more spaces separating the threads of the hole from the first longitudinal row of holes and the threads of the hole from the second longitudinal row of holes, with the threads of the holes of the first longitudinal row of holes and the threads of the holes of the second longitudinal row of holes being adjacent to the one or more spaces throughout a length of the plate, and
wherein the plate is formed of a plurality of segments, each segment including an equal number of holes from each of the longitudinal rows of holes.

2. The system of claim 1, wherein the attachment members include a variable angle locking feature.

3. The system of claim 2, wherein the variable angle locking feature ranges from a 5 degree cone of angulation to a 20 degree cone of angulation.

4. The system of claim 1, wherein the attachment members are configured to engage the plate at a selected angle relative to a central axis of each of the plurality of holes.

5. The system of claim 1, wherein the attachment members include bilaterally angled screws.

6. The system of claim 1, wherein the holes include a plurality of threaded columns separated by non-threaded recesses.

7. The system of claim 1, wherein the attachment members comprise any one of a trauma screw, an arch screw, or a spine screw.

8. The system of claim 1, wherein the holes are perpendicular to the central longitudinal axis of the plate.

9. The system of claim 1, wherein the holes are angled at an angle of approximately 10 to 30 degrees of lateral outward angulation with respect to the plate.

10. The system of claim 6, wherein the plate includes a contoured surface, the contoured surface forming a node around each hole of the plurality of holes.

11. The system of claim 1, wherein an angle between adjacent holes in each segment ranges from about 30 degrees to about 60 degrees relative to the central longitudinal axis of the plate.

12. The system of claim 3, wherein a distance between recesses formed on opposite sides of the plate ranges from about 5 millimeters to about 6 millimeters and a distance between nodes on opposite sides of the plate ranges from about 8 millimeters to about 10 millimeters.

13. The system of claim 1, wherein a distance measured between centers of a pair of laterally adjacent holes of the plurality of holes ranges from about 2 millimeters to about 5 millimeters.

14. The system of claim 1, wherein one or more of the holes of the first longitudinal row and the holes of the second longitudinal row are angled in at least one of a direction that is parallel to the central longitudinal axis of the plate and in a direction that is perpendicular to the central longitudinal axis of the plate.

15. The system of claim 1, further comprising an inserter tool configured to implant the plate in the lateral mass.

16. The system of claim 1, further comprising an access tube defining a channel therein, the access tube being configured to receive the plate and the attachment members therethrough.

17. The system of claim 16, wherein the access tube comprises a cut-out formed on a distal end of the access tube.

18. The system of claim 1, further comprising a mesh material extending from one of the upper surface and the lower surface.

19. The system of claim 18, wherein the mesh material defines rhombal-shaped openings therein.

20. The system of claim 18, wherein the mesh material forms a base of one or more of the holes of the first longitudinal row and the holes of the second longitudinal row.

21. The system of claim 10, wherein a radius of curvature of the node ranges from about 2.5 millimeters to about 3.5 millimeters, and a radius of curvature of the recesses ranges from about 1 millimeters to about 1.5 millimeters.

22. The system of claim 1, wherein the threads of at least one of the holes in the first longitudinal row of holes intersects a line that extends between an axis of the at least one hole and an axis of the adjacent hole from the second longitudinal row of holes.

23. A vertebral plating system, comprising:
a plate having an upper surface, a lower surface, and a plurality of holes that extend from the upper surface to the lower surface, the plate being configured to extend along at least one lateral mass of each of adjacent vertebral levels such that two or more of the plurality of holes define a plurality of fixation points at each lateral mass of the adjacent vertebral levels; and
a plurality of attachment members configured to be inserted through the plurality of holes in the plate and into the lateral masses of each of the vertebral levels to fix the plate to the vertebral levels, wherein the plurality of holes are arranged in two longitudinal rows such that the holes of a first longitudinal row of holes are offset with respect to a second longitudinal row of holes, with the first longitudinal row having a first central axis and the second longitudinal row having a second central axis, and a number of holes in the first longitudinal row is equal to a number of holes of the second longitudinal row, wherein a central longitudinal axis of the plate passes through at least a portion of each of the plurality of holes, wherein the upper surface includes one or more spaces formed between a hole from the first longitudinal row of holes and an adjacent hole from the second longitudinal row of holes, the one or more spaces being defined by a portion of the upper surface and lying in a common plane with a plane of the upper surface, the one or more spaces extending between an outermost point of each of the holes across the central longitudinal axis of the plate, wherein one or more of the holes is threaded such that the threads of at least one of the holes are positioned adjacent to the one or more spaces to increase the strength of the plate, the one or more spaces separating the threads of the hole from the first longitudinal row of holes and the threads of the hole from the second longitudinal row of holes, with the threads of the holes of the first longitudinal row of holes and the threads of the holes of the second longitudinal row of holes being adjacent to the one or more spaces throughout a length of the plate, and wherein the plate is formed of a plurality of segments, each segment including one hole from each of the longitudinal rows of holes.

24. A vertebral plating system, comprising:

a plate having an upper surface, a lower surface, and a plurality of holes that extend from the upper surface to the lower surface, the plate being configured to extend along at least one lateral mass of each of adjacent vertebral levels such that two or more of the plurality of holes define a plurality of fixation points at each lateral mass of the adjacent vertebral levels; and a plurality of attachment members configured to be inserted through the plurality of holes in the plate and into the lateral masses of each of the vertebral levels to fix the plate to the vertebral levels, wherein the plurality of holes are arranged in two longitudinal rows such that the holes of a first longitudinal row of holes are offset with respect to a second longitudinal row of holes, with the first longitudinal row having a first central axis and the second longitudinal row having a second central axis, wherein a central longitudinal axis of the plate passes through at least a portion of each of the plurality of holes, wherein the upper surface includes one or more spaces formed between a hole from the first longitudinal row of holes and an adjacent hole from the second longitudinal row of holes, the one or more spaces being defined by a portion of the upper surface and lying in a common plane with a plane of the upper surface, the one or more spaces extending between an outermost point of each of the holes across the central longitudinal axis of the plate, wherein the plate is formed of a plurality of segments, each segment including one hole from each of the longitudinal rows of holes, wherein the holes include a plurality of threaded columns separated by non-threaded recesses, wherein the plate includes a contoured surface, the contoured surface forming a node around each hole of the plurality of holes, and wherein a radius of curvature of the node ranges from about 2.5 millimeters to about 3.5 millimeters, and a radius of curvature of the recesses ranges from about 1 millimeters to about 1.5 millimeters.

* * * * *